(12) United States Patent
Vodyanyk et al.

(10) Patent No.: US 9,771,561 B2
(45) Date of Patent: *Sep. 26, 2017

(54) METHOD OF MAKING PRIMATE CELLS EXPRESSING APELIN RECEPTOR THAT HAVE MESANGIOBLAST POTENTIAL

(71) Applicant: Wisconsin Alumni Research Foundation, Madison, WI (US)

(72) Inventors: Maksym A. Vodyanyk, Madison, WI (US); Igor I. Slukvin, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,130

(22) Filed: Dec. 12, 2014

(65) Prior Publication Data

US 2015/0175971 A1    Jun. 25, 2015

Related U.S. Application Data

(63) Continuation of application No. 12/726,814, filed on Mar. 18, 2010, now abandoned, which is a continuation-in-part of application No. 12/554,696, filed on Sep. 4, 2009, now abandoned, which is a continuation of application No. 12/024,770, filed on Feb. 1, 2008, now Pat. No. 7,615,374.

(60) Provisional application No. 60/974,980, filed on Sep. 25, 2007, provisional application No. 60/989,058, filed on Nov. 19, 2007.

(51) Int. Cl.
*C12N 5/00* (2006.01)
*C12N 5/0775* (2010.01)
*C12N 5/0789* (2010.01)
*C12N 5/071* (2010.01)

(52) U.S. Cl.
CPC .......... *C12N 5/0662* (2013.01); *C12N 5/069* (2013.01); *C12N 5/0647* (2013.01); *C12N 5/0692* (2013.01); *C12N 2500/38* (2013.01); *C12N 2500/44* (2013.01); *C12N 2500/90* (2013.01); *C12N 2501/115* (2013.01); *C12N 2501/125* (2013.01); *C12N 2501/135* (2013.01); *C12N 2501/145* (2013.01); *C12N 2501/155* (2013.01); *C12N 2501/165* (2013.01); *C12N 2501/23* (2013.01); *C12N 2502/1394* (2013.01); *C12N 2506/02* (2013.01); *C12N 2506/45* (2013.01); *C12N 2533/54* (2013.01); *C12N 2533/70* (2013.01); *C12N 2533/78* (2013.01)

(58) Field of Classification Search
USPC ....................................................... 435/325
See application file for complete search history.

(56) References Cited

U.S. PATENT DOCUMENTS

| | | | |
|---|---|---|---|
| 7,615,374 B2 | 11/2009 | Vodyanyk et al. |
| 2006/0008902 A1 | 1/2006 | Pike et al. |
| 2008/0025955 A1 | 1/2008 | Nakao et al. |
| 2010/0015705 A1 | 1/2010 | Vodyanyk et al. |
| 2010/0261274 A1 | 10/2010 | Vodyanyk et al. |

FOREIGN PATENT DOCUMENTS

| | | |
|---|---|---|
| WO | 2007027156 A1 | 3/2007 |
| WO | 2008020815 A1 | 2/2008 |

OTHER PUBLICATIONS

Vodyanik (Blood, 2005, vol. 105, p. 617-626).*
Saint-Geniez (Gene Expression Patterns, 2003, vol. 3, p. 467-472).*
Tonlorenzi (Curr. Protoc. Stem Cell Biol., Dec. 2007, Chapt. 2B).*
Vodyanik (Cell Stem Cell, 2010, vol. 7, p. 718-729).*
Tedesco (Sci. Translational Med., Jun. 27, 2012, vol. 4, No. 140, 140ra89, p. 1-15).*
Bonfanti (Nature Communications, 2015, vol. 6, No. 6364, p. 1-13).*
Mesoangioblast definition, Wikipedia, 2016.*
endothelial progenitor cells description by Wikipedia, 2017.*
endothelial progenitor cells description by R&D Systems, 2017.*
Barberi, T. et al. "Derivation of multipotent mesenchymal precursors from human embryonic stem cells," PLoS Med. 2:e161(2005).
Choi, Kyung—Dal, et al. "Hematopoietic and endothelial differentiation of human induced pluripotent stem cells" Stem Cells 27.3 (2009): 559-567.
De Peppo, Giuseppe Maria et al., "Human embryonic mesodermal progenitors highly resemble human mesenchymal stem cells and display high potential for tissue engineering applications," Tissue Engineering, Part A, vol. 16, No. 7, pp. 2161-2182 (Mar. 10, 2010).
Docheva, D. et al., "Mesenchymal Stem Cells and Their Cell Surface Receptors," Current Rheumatology Reviews, vol. 4, pp. 1-6 (2008).
Karlsson, Camilla et al., "Human embryonic stem cell-derived mesenchymal progenitors-Potential in regenerative medicine," Stem Cell Research, vol. 3, No. 1, pp. 39-50 (Jul. 2009).
Korhonen, M. "Culture of human mesenchymal stem cells in serum-free conditions: no breakthroughs yet," Eur. J. Haematol. 77:167 (2007).
Koyanagi, Masamichi, et al. "Sox2 transduction enhances cardiovascular repair capacity of blood-derived mesoangioblasts." Circulation research 106.7 (2010): 1290-1302.
Lian, Qizhou et al., "Functional mesenchymal stem cells derived from human induced pluripotent stem cells attenuate limb ischemia in mice," Circulation, vol. 121, No. 9, pp. 1113-1123 (Mar. 9, 2010).
Mendes, Sandra C. et al., "Mesenchymal progenitor cells localize within hematopoietic sites throughout ontogeny," Development, vol. 132, No. 5, pp. 1127-1136 (Mar. 2005).

(Continued)

*Primary Examiner* — Michael Wilson
(74) *Attorney, Agent, or Firm* — Quarles & Brady LLP

(57) ABSTRACT

Methods for obtaining multipotent Apelin receptor-positive lateral plate mesoderm cells, mesenchymal stem cells, and mesangioblasts under serum-free conditions are disclosed.

6 Claims, 19 Drawing Sheets

(56) References Cited

OTHER PUBLICATIONS

Meuleman, Nathalie, et al. "Human marrow mesenchymal stem cell culture: serum—free medium allows better expansion than classical α—MEM medium." European journal of haematology 76.4 (2006): 309-316.

Meuleman, N. et al., "Human marrow mesenchymal stem cell culture: serum-free medium allows better expansion than classical alpha-minimal essential medium (MEM)," Eur. J. Haematol. 77:168 (2007).

Nowak, Kristen. "Chapter 15 Therapeutic Approaches for the Sarcomeric Protein Diseases," The Sarcomere and Skeletal Muscle Disease, edited by Nigel Laing, Landes Bioscience (2008).

Olivier, E. et al., "Differentiation of human embryonic stem cells into mesenchymal stem cells," Blood (47th Annual Meeting of the American Society of Hematology) 106:Abstract 1389 (2005).

Olivier, E. et al., "Differentiation of human embryonic stem cells into bipotent mesenchymal stem cells," Stem Cells 24:1914-1922 (2006).

Saint-Geniez, Magali, et al. "The msr/apj gene encoding the apelin receptor is an early and specific marker of the venous phenotype in the retinal vasculature." Gene expression patterns 3.4 (2003): 467-472.

Sotiropoulou, P. et al., "Cell culture medium composition and translational adult bone marrow-derived stem cell research," Stem Cells 24:1409-1410 (2006).

Trivedi, P. and Hematti, P., "Simultaneous generation of CD34+ primitive hematopoietic cells and CD56+ mesenchymal stem cells from human embryonic stem cells cocultured with murine OP9 stromal cells," Exp. Hematol. 35:146-154 (2007).

Trivedi, P. And Hematti, P., "Derivation and immunological characterization of mesenchymal stromal cells from human embryonic stem cells," Exp. Hematol. 36:350-359 (2008).

Vodyanik, Maxim A. et al., "A mesoderm-derived precursor for mesenchymal stem and endothelial cells," Cell Stem Cell, vol. 7, No. 6, pp. 718-729 (Dec. 3, 2010).

Vodyanik, M. et al., "Human embryonic stem cell-derived CD34+ cells: efficient production in the coculture with OP9 stromal cells and analysis of lymphohematopoietic potential," Blood 105:617-626 (2005).

PCT International Search Report and Written Opinion, PCT/US2011/028700, Sep. 19, 2011.

Lancrin, Christophe, et al. "The haemangioblast generates haematopoietic cells through a haemogenic endothelium stage." Nature 457.7231 (2009): 892-895.

Schubert, C. J. "Muscular dystrophy meets the mesangioblast," Nature Medicine, Aug. 2003, p. 999.

* cited by examiner

METHOD OF MAKING PRIMATE CELLS EXPRESSING APELIN RECEPTOR THAT HAVE MESANGIOBLAST POTENTIAL

CROSS-REFERENCE TO RELATED APPLICATIONS

This application is a continuation of U.S. patent application Ser. No. 12/726,814, filed Mar. 18, 2010, which is a continuation-in-part application of U.S. patent application Ser. No. 12/554,696, abandoned, which is a continuation application of U.S. patent application Ser. No. 12/024,770, now U.S. Pat. No. 7,615,374, issued on Nov. 10, 2009, which claims the benefit of U.S. Provisional Patent Application No. 60/974,980, filed Sep. 25, 2007; and U.S. Provisional Patent Application No. 60/989,058, filed Nov. 19, 2007, each of which is incorporated herein by reference as if set forth in its entirety.

STATEMENT REGARDING FEDERALLY SPONSORED RESEARCH OR DEVELOPMENT

This invention was made with government support under RR052085, HD044067, and HL081962 awarded by the National Institutes of Health. The government has certain rights in the invention.

BACKGROUND

The invention relates generally to clonal primate mesenchymal progenitors and to mesenchymal stem cell (MSC) lines and methods for identifying and generating such cells, and more particularly to methods for generating clonal mesenchymal progenitors and MSC lines under serum-free conditions. The invention further relates to a population of shared endothelial- and mesenchymal cell precursors and methods for identifying and generating such cells. The invention furthermore relates to a population of cells comprising lateral plate mesoderm cells and methods for their generation and isolation from cultured pluripotent stem cells.

During embryonic development of animals, gastrulation forms three germ layers, i.e., endoderm, ectoderm, and mesoderm, that each give rise to distinct bodily cells. Mesoderm develops from primitive streak, a transient embryonic structure formed at the onset of gastrulation. Nascent mesoderm transitionally differentiates into paraxial mesoderm, intermediate mesoderm, and lateral plate mesoderm. Paraxial mesoderm gives rise to axial skeleton, and skeletal muscles. Intermediate mesoderm forms the urogenital system. Lateral plate mesoderm gives rise to the circulatory system, including blood cells, vessels, and heart, and forms the viscera and limbs. Extraembryonic mesoderm is located outside the developing embryo. Evidence suggests that extraembryonic mesoderm is derived from the primitive streak during gastrulation (Boucher and Pedersen, Reprod. Fertil. Dev. 8:765 (1996)). Extraembryonic mesoderm gives rise to several tissues that provide the embryo with nutrients, a means of waste disposal, and mechanical protection.

Both lateral plate and extraembryonic mesoderm can generate endothelial and blood cells and express FOXF1, HAND1, HAND2, GATA-2, BMP4, and WNT5a, expression of which is low or undetectable in paraxial and intermediate mesoderm (Mahlapuu et al., Development. 128 (2):155 (2001); Firulli et al., Nat. Genet. 18 (3):266 (1998); Morikawa et al., Circ. Res. 103 (12):1422 (2008); Kelley et al., Dev. Biol. 165:193 (1994); Silver et al., Blood 89 (4):1154 (1997); Fujiwara et al., Proc. Natl. Acad. Sci. 98 (24):13739 (2001); Takada et al., Genes Dev. 8 (2):174 (1994)). Distinctive markers for lateral plate and extraembryonic mesoderm remain to be elucidated. A recent finding by Bosse et al. suggests that IRX3 is expressed in lateral plate mesoderm but not in extraembryonic mesoderm (Bosse et al., Mech. Dev. 69 (1-2):169 (1997)). For the purposes of this application, the term lateral plate is used to describe both tissues.

Certain committed mesodermal progenitors can give rise to cells of more than one lineage. Example of such progenitors includes hemangioblasts, which can give rise to both hematopoietic- and endothelial cells. Choi K, et al., "A common precursor of hematopoietic and endothelial cells," Development 125:725 (1998).

MSCs can differentiate into at least three downstream mesenchymal cell lineages (i.e., osteoblasts, chondroblasts, and adipocytes). To date, no unique MSC marker has been identified. As such, morphological and functional criteria are used to identify these cells. See, Horwitz E, et al., "Clarification of the nomenclature for MSC: the International Society for Cellular Therapy position statement," Cytotherapy 7:393 (2005); and Dominici M, et al., "Minimal criteria for defining multipotent mesenchymal stromal cells. The International Society for Cellular Therapy position statement," Cytotherapy 8:315 (2006). Because MSCs can differentiate into many cell types, the art contemplates methods for differentiating MSCs for cell-based therapies, for regenerative medicine and for reconstructive medicine.

Typically, MSCs are isolated from adult bone marrow, fat, cartilage and muscle. Pittenger F, et al., "Multilineage potential of adult human mesenchymal stem cells," Science 284:143-147 (1999); Zuk P, et al., "Multilineage cells from human adipose tissue: implications for cell-based therapies," Tissue Eng. 7:211-228 (2001); and Young H, et al., "Human reserve pluripotent mesenchymal stem cells are present in the connective tissues of skeletal muscle and dermis derived from fetal, adult, and geriatric donors," Anat. Rec. 264:51-62 (2001). MSCs have also been isolated from human peripheral blood. Kassis I, et al., "Isolation of mesenchymal stem cells from G-CSF-mobilized human peripheral blood using fibrin microbeads," Bone Marrow Transplant. 37:967-976 (2006). MSCs can also be isolated from human neonatal tissue, such as Wharton's jelly (Wang H, et al., "Mesenchymal stem cells in the Wharton's jelly of the human umbilical cord," Stem Cells 22:1330-1337 (2004)), human placenta (Fukuchi Y, et al., "Human placenta-derived cells have mesenchymal stem/progenitor cell potential," Stem Cells 22:649-658 (2004)); and umbilical cord blood (Erices A, et al., "Mesenchymal progenitor cells in human umbilical cord blood," Br. J. Haematol. 109:235-242 (2000)) and human fetal tissues (Campagnoli C, et al., "Identification of mesenchymal stem/progenitor cells in human first-trimester fetal blood, liver, and bone marrow," Blood 98:2396-2402 (2001)).

The art is limited by an inability to isolate sufficient MSCs for subsequent differentiation and use. Where suitable donors are available, the invasive procedures required to isolate even a limited number of cells present risks to donors. It also remains difficult to maintain isolated MSCs in long-term culture and to maintain such cultures free of bacterial or viral contamination.

Efforts to devise methods for differentiating embryonic stem cells (ESCs) including human ESCs (hESCs) to MSCs either have required culturing the cells in a medium containing potentially contaminating serum or have yielded cells that retain characteristics of undifferentiated hESCs.

For example, Barberi et al. differentiated hESCs to MSCs on mitotically-inactivated mouse stromal cell lines feeder cells) with 20% heat-inactivated fetal bovine serum (FBS) in alpha MEM medium for 40 days. Barberi T, et al. "Derivation of multipotent mesenchymal precursors from human embryonic stem cells," PLoS Med. 2:e161 (2005). Cells were harvested and assayed for CD73, and CD73+ cells were then plated in the absence of the feeder cells with 20% FBS in alpha MEM for 7 to 10 days. Barberi et al. differentiated the MSCs into adipogenic cells, chondrogenic cells, osteogenic cells and myogenic cells.

Likewise, Olivier et al. differentiated hESCs to MSCs by plating raclures (i.e., spontaneously differentiated cells that appear in hESC culture in the center or at the edges of colonies) with D10 medium (DMEM, 10% FBS, 1% penicillin/streptomycin and 1% non-essential amino acids) changed weekly until a thick, multi-layer epithelium developed. Olivier E, et al., "Differentiation of human embryonic stem cells into bipotent mesenchymal stem cells," Stem Cells 24:1914-1922 (2006). After approximately four weeks, MSCs were isolated by dissociating the epithelium with a mixture of trypsin, collagenase type IV and dispase for four to six hours, followed by re-plating in D10 medium. Olivier et al.'s MSCs grew robustly, had stable karyotypes, were contact inhibited, senesced after twenty passages and differentiated into adipogenic and osteogenic cells. Olivier et al. did not report that the cells differentiated into chondroblasts. Unlike Barberi et al., Olivier et al. did not require feeder cells to support differentiation of hESC to MSCs. However, Olivier et al.'s MSCs were SSEA-4 positive, suggesting that these MSCs expressed cell surface markers characteristic of hESC.

Pike & Shevde differentiated hESCs to MSCs via embryoid bodies (EBs) incubated for ten to twelve days in a mesenchymal-specific medium (MesenCult® medium with 10% FBS; alpha MEM with glutamine and nucleosides; or DMEM with glucose and glutamine, replaced every two days). US Patent Publication No. 2006/0008902. The EBs were digested, and pre-mesenchymal cells were cultured to 80% confluence. The cells were trypsinized and passaged three times in mesenchymal-specific medium.

Meuleman et al. reported culturing MSCs in a serum-free medium; however, it was later discovered that the medium did in fact contain animal serum as a component. Meuleman N, et al., "Human marrow mesenchymal stem cell culture: serum-free medium allows better expansion than classical alpha-minimal essential medium (MEM)," Eur. J. Haematol. 76:309-316 (2006); and Meuleman N, et al., "Human marrow mesenchymal stem cell culture: serum-free medium allows better expansion than classical alpha-minimal essential medium (MEM)," Eur. J. Haematol. 77:168 (2007); but see, Korhonen M, "Culture of human mesenchymal stem cells in serum-free conditions: no breakthroughs yet," Eur. J. Haematol. 77:167 (2007).

Those methods cultured and differentiated MSCs in serum-containing medium. Serum-free conditions for culturing and differentiating MSCs, if defined, would reduce variation among batches and eliminate a risk of infection transmitted by xenogenic by-products and pathogens. Sotiropoulou P, et al., "Cell culture medium composition and translational adult bone marrow-derived stem cell research," Stem Cells 24:1409-1410 (2006).

For the foregoing reasons, there is a need for new methods for obtaining early mesenchymal progenitors and MSCs, especially when derived under serum-free conditions.

Mesoderm and the neural crest can both give rise to mesenchymal precursors during embryonic development. Dennis, J. E., and P. Charbord, "Origin and differentiation of human and murine stroma," Stem Cells 20:205-214 (2002); Takashima, Y, et al., "Neuroepithelial cells supply an initial transient wave of MSC differentiation," Cell 129:1377-1388 (2007). While conditions for generating MSCs of neural crest origin from embryonic stem cells have been described, Takashima et al., supra; Lee, G, et al., "Isolation and directed differentiation of neural crest stem cells derived from human embryonic stem cells," Nat Biotechnol 25:1468-1475 (2007), it is not known how to generate MSCs from mesoderm.

For the foregoing reasons, there is a need for new methods for obtaining early mesenchymal progenitors and MSCs, particularly under serum-free conditions. Further, there is a need to identify and generate mesoderm-derived MSCs as well as early mesodermal progenitors that can give rise to MSCs during differentiation of pluripotent stem cells into MSCs.

BRIEF SUMMARY

The invention generally relates to a newly identified common mesenchymal and endothelial cell precursor, i.e., mesangioblasts, derived from in vitro-differentiated stem cells.

In a first aspect, the invention is summarized in that a method of generating a clonal population of primate MSCs includes the steps of culturing a heterogeneous, single-cell suspension of primate cells that contains mesenchymal progenitors in a serum-free, semi-solid medium containing between about 5 and about 100 ng/ml bFGF until independent colonies form, and culturing, one of the independent colonies in a serum-free, liquid medium containing between about 5 and about 100 ng/ml, or at about 5 ng/ml, or between about 20 and about 100 ng/ml, bFGF to obtain an substantially pure clonal population of MSCs.

The heterogeneous suspension for use in the method can be obtained, for example, by differentiating pluripotent cells from a primate (e.g., human), such as ESCs or induced pluripotent stem (iPS) cells, in culture until cells in the culture are mesenchymal progenitors. This can be accomplished by co-culturing the pluripotent cells with bone marrow stromal cells in a medium that supports differentiation as described herein for at least two to five days, or by dissociating EBs, which can themselves be obtained by culture of pluripotent cells using well-known methods, and then suspending the cells as a single cell suspension. The bone marrow stromal cells can be mouse OP9 cells. A heterogeneous suspension substantially free of some or all cells not derived by in vitro differentiation of pluripotent cells (especially co-cultured bone marrow cells) can be obtained by depleting those cells from the suspension. These cells can be depleted from the suspension before use, for example, by non-covalently binding the cells to be depleted to paramagnetic monoclonal antibodies specific for the epitopes on the cells to be depleted and then segregating the antibody-bound cells with a magnet. Cells in a suspension obtained from pluripotent cells can express at least MIXL1 and T (BRACHYURY).

The medium can be rendered semi-solid by including about 1% methylcellulose in the medium. The medium can optionally contain between about 10 and about 20 ng/ml PDGF-BB. The suspension can be cultured for between about ten to about twenty days or more to produce the colonies.

Mesenchymal progenitors are identified as having been present in the suspension if mesenchymal colonies form during culture in the serum-free, semi-solid medium supplemented with bFGF. An example of such bFGF-dependent colony-forming assay for detecting mesenchymal progenitor is described in U.S. Pat. No. 7,615,374, incorporated herein as if set forth in its entirety. The colonies obtained in the colony-forming assay can be identified as mesenchymal by their expression of at least a plurality of FOXF1, MSX1, MSX2, SNAI1, SNAI2, SOX9 and RUNX2. Characteristics of the colonies include functional, morphological and phenotypical characteristics and gene expression profile. Functional characteristics of the colonies include (1) growth stimulation by factors that promote mesenchymal cell growth (e.g., PDGF-BB, EGF and TGF-alpha) and growth suppression by factors involved in mesodermal differentiation (e.g., VEGF, TGF-beta and Activin A); (2) differentiation into osteogenic, chondrogenic or adipogenic cell lineages; and (3) differentiation into endothelial cells. Morphological characteristics of the colonies include (1) tight packing of cells to form round (i.e., spherical) aggregates measuring 100-500 µm in diameter; (2) colony formation through establishing tightly packed structures (cores) that further develop into compact spheroid colonies; and (3) even after prolonged culture, lack of dense outer cell layer and irregular inner structure, which are characteristics of EBs. Phenotypical characteristics of the colonies include (1) expression of CD44, CD56, CD105 and CD140a (PDGFRA), CD146, but not hematoendothelial surface markers (i.e., CD31, CD43, CD45 and VE-cadherin); (2) expression of FOXF1, MSX1, MSX2, SNAI1, SNAI2, SOX9 and RUNX2; and (3) expression of vimentin, alpha smooth muscle actin, and desmin.

The mesenchymal colonies thus formed in the method can be further cultured in the presence of an extracellular matrix protein, such as Matrigel®, collagen, gelatin or fibronectin, as well as combinations thereof.

The invention is further summarized as a substantially pure population of clonally-derived MSC lines produced from the methods described above that are positive for at least CD44, CD56, CD 73, CD105, CD140a, and CD146, but negative for CD31, CD43, CD45 and VE-cadherin.

The described embodiments have many advantages, including that mesenchymal progenitors and MSCs obtained in the methods may be used to treat diseases associated with bone, cartilage and fat cells.

It is also an advantage that a clonal population of MSCs can be obtained from a single mesenchymal colony.

It is also an advantage that the cells obtained in the methods can easily be selected for further expansion because the mesenchymal progenitors have high proliferation potential and form large colonies.

It is yet another advantage that cells obtained in the methods can be tolerant or tolerogenic to allo- and auto-immune response on transplantation.

It is still another advantage that the cells obtained in the methods can differentiate into at least osteogenic, chondrogenic and adipogenic lineages.

It is still another advantage that mesenchymal colonies obtained in the methods possess angiogenic potential.

The invention is further summarized as a population of in vitro-derived Apelin receptor-positive (APLNR$^+$) lateral plate mesoderm cells. These cells can be isolated from mixed populations of differentiating pluripotent stem cells based on expression of the Apelin receptor (APLNR). These cells can differentiate into cells of the body wall and viscera and give rise to mesangiogenic mesenchymal and hemangiogenic blast colonies in semisolid media cultures in the presence of bFGF. The APLNR$^+$ cells express transcripts characteristic of mesoderm, specifically lateral plate mesoderm.

It is still another advantage of the invention that MSCs obtained by the claimed methods are of mesodermal origin and can be derived from APLNR$^+$ cells enriched in lateral plate mesoderm cells.

These and other features, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

BRIEF DESCRIPTION OF THE DRAWINGS

FIG. 1A depicts MB and HB colony morphologies following growth in semisolid media for 3, 5, 7, and 12 days. FIG. 1B depicts the kinetics of FGF-dependent colony formation. Bars represent standard deviation of four independent experiments. Depending on whether the hESC-derived single cells are initially co-cultured with OP9 cells for 2 days or 3 days, they assume either MB or HB potential. FIG. 1C illustrates that bFGF, but not PDGF or VEGF alone, supports both MB and HB colony formation. The data are represented as mean±SD (n=4). The asterisk indicates statistical significance (p<0.01) between cultures containing FGF alone and FGF in combination with either PDGF or VEGF. FIG. 1D illustrates the differentiation potential of MB-derived and HB-derived colonies after coculture with OP9 cells for 4 days. Flow cytometry demonstrated that MB colony-derived cells collected on day 12 of clonogenic culture gave rise to CD146$^+$CD31$^-$ mesenchymal and CD31$^+$CD43$^-$ endothelial cells, while HB colony-derived cells gave rise to CD31$^+$CD43$^-$ endothelial cells and CD43$^+$ hematopoietic lineage cells. FIG. 1E illustrates immunostaining analysis of cell clusters developed from a single MB (top, scale bar, 100 µm) and HB (bottom, scale bar, 50 µm) colony collected on day 5 of clonogenic culture. Cells were identified as CD144$^+$ (also known as VE-cadherin) CD43$^-$ endothelial, CD43$^+$ hematopoietic, and calponin$^+$ CD144$^-$ mesenchymal. The scale bars represent 100 µm. Colonies developed from cell clusters of a single MB colony generate calponin$^+$CD144(VE-cadherin)$^-$ mesenchymal cells and CD144(VE-cadherin)$^+$calponin$^-$ endothelial cells (upper panel). Colonies developed from cell clusters developed from a single HB colony generate CD43$^+$ hematopoietic and CD144(VE-cadherin)$^+$CD43$^-$ endothelial cells (lower panel).

FIG. 2 illustrates microarray analysis of gene expression in hESCs co-cultured with OP9 cells from day 0 (H1) to day 7.

FIG. 3 illustrates analysis of APLNR$^+$ cells.

FIG. 4 illustrates the gene expression profiles of APLNR+ cells, APLNR− cells, cores, colonies, and a mesenchymal stem cell (MSC) line (at passages p1 and p5) obtained from H1 hESCs differentiated for 2 (D2) or 3 (D3) days by coculture with OP9 cells.

DESCRIPTION OF EXEMPLARY EMBODIMENTS

Figure 1A:
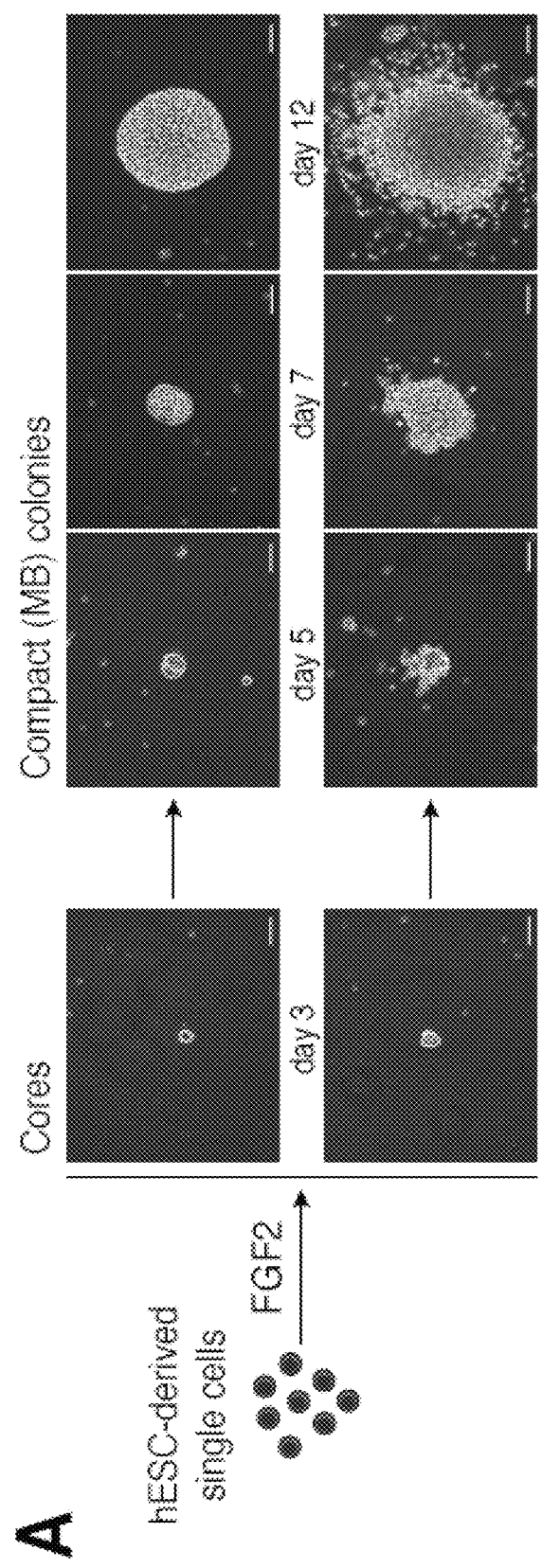
FIG. 1A-E illustrate the properties of two types of hESC-derived colonies, i.e., mesenchymal colonies derived from mesangioblasts (MB) and blast colonies derived from hemangioblasts (HB).

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein. It is commonly understood by one of ordinary skill in the art that "lack of expression" of a gene or the absence of a certain marker on a cell refers to an inability to detect such gene or marker expression using methods known in the art at the time of filing. It cannot be ruled out that more sensitive methods could detect low levels of expression of such genes or markers.

In describing the embodiments and claiming the invention, the following terminology is used in accordance with the definitions set out below.

As used herein, "about" means within 5% of a stated concentration.

As used herein, "clonal" means a population of cells cultured from a single cell, not from an aggregate of cells. Cells in a "clonal population" display a substantially uniform pattern of cell surface markers and morphology and are substantially genetically identical.

As used herein, an "embryoid body" or an "EB," is an aggregate of cells derived from pluripotent cells, such as ESCs or iPS cells, where cell aggregation can be initiated by hanging drop, by plating upon non-tissue culture-treated plates or spinner flasks (i.e., low attachment conditions); and any method that prevents the cells from adhering to a surface to form typical colony growth. EBs appear as rounded collections of cells and contain cell types derived from all three germ layers (i.e., the ectoderm, mesoderm and endoderm). Methods for generating EBs are well-known to one having ordinary skill in the art. See, Itskovitz-Eldor J, et al., "Differentiation of human embryonic stem cells into embryoid bodies compromising the three embryonic germ layers," Mol. Med. 6:88-95 (2000); Odorico J, et al., Stem Cells 19:193-204 (2001); and U.S. Pat. No. 6,602,711, each of which is incorporated herein by reference as if set forth in its entirety.

As used herein, "serum-free" means that neither the culture nor the culture medium contains serum or plasma, although purified or synthetic serum or plasma components (e.g., FGFs) can be provided in the culture in reproducible amounts as described below.

As used here, a "substantially pure population" means a population of derived cells that contains at least 99% of the desired cell type. Cell purification can be accomplished by any means known to one of ordinary skill in the art. For example, a substantially pure population of cells can be achieved by growth of cells or by selection from a less pure population, as described herein.

As used herein, "pluripotent cells" means a population of cells capable of differentiating into all three germ layers and becoming any cell type in the body. Pluripotent cells express a variety of cell surface markers, have a cell morphology characteristic of undifferentiated cells and form teratomas when introduced into an immunocompromised animal, such as a SCID mouse. Teratomas typically contain cells or tissues characteristic of all three germ layers.

As used herein, "multipotent" cells are more differentiated than pluripotent cells, but are not permanently committed to a specific cell type. Pluripotent cells therefore have a higher potency than multipotent cells.

As used herein, "induced pluripotent stem cells" or "iPS cells" are cells that are differentiated, somatic cells reprogrammed to pluripotency. The cells are substantially genetically identical to their respective differentiated somatic cell of origin and display characteristics similar to higher potency cells, such as ES cells. See, Yu J, et al., "Induced pluripotent stem cell lines derived from human somatic cells," Science 318:1917-1920 (2007), incorporated herein by reference as if set forth in its entirety.

As used herein, a "mesenchymal stem cell" (MSC) is a cell capable of differentiating into the skeletal cell lineages (i.e., osteoblasts, chondroblasts and adipocytes). As noted above, no unique MSC marker has been identified. As such, morphological and functional criteria well-known to those of ordinary skill in the art are used to identify these cells. See, Horwitz et al., supra; Dominici et al., supra; Trivedi P & Hematti P, "Derivation and immunological characterization of mesenchymal stromal cells from human embryonic stem cells," Exp. Hematol. Jan. 5, 2008 [Epub ahead of print]; Trivedi P & Hematti P, "Simultaneous generation of CD34+ primitive hematopoietic cells and CD56+ mesenchymal stem cells from human embryonic stem cells cocultured with murine OP9 stromal cells," Exp. Hematol. 35:146-154 (2007); and US Published Patent Application No. 2006/0008902, each of which is incorporated herein by reference as if set forth in its entirety. MSCs produced by the methods described herein can be characterized according to phenotypic criteria. For example, MSCs can be recognized by their characteristic mononuclear ovoid, stellate shape or spindle shape, with a round to oval nucleus. The oval elongate nuclei typically have prominent nucleoli and a mix of hetero- and euchromatin. These cells have little cytoplasm, but many thin processes that appear to extend from the nucleus. It is believed that MSCs will typically stain for one, two, three or more of the following markers: CD106

(VCAM), CD73, CD146, CD166 (ALCAM), CD29, CD44 and alkaline phosphatase, while being negative for hematopoietic lineage cell markers (e.g., CD14 or CD45) and endothelial lineage cell markers (e.g., CD31 and VE-cadherin). MSCs may also express STRO-1 as a marker.

As used herein, a "mesangioblast" is a progenitor for MSCs as well as endothelial cells.

As used herein, a "mesenchymal colony" is a colony composed of mesenchymal cells originating from mesangioblasts.

As used herein, a "hemangioblast" is a precursor to blood cells as well as endothelial cells.

As used herein, a "blast colony" is a colony composed of predominantly hematopoietic cells originating from hemangioblasts.

As used herein, "mesendoderm" is a tissue that gives rise to mesoderm and endoderm.

As used herein, "mesoderm" is a cell subset that expresses KDR and PDGFRa to much greater level than POU4F1, SOX1, and PAX6 (neural crest and neuroectoderm), LAMA3, KRT14, and KRT10 (surface ectoderm), CGA and PLAC1 (trophectoderm) FOXA1, FOXA2, APOA1, TMPRSS2, TTR1, and AFP (endoderm), and SOX2 and DPPA2 (undifferentiated hESCs).

As used herein, "lateral plate mesoderm" is a subset of mesoderm that expresses at least FOXF1 and HAND1 but lacks expression of MEOX1 and TCF15 (paraxial mesoderm), PAX2 and PAX8 (intermediate mesoderm), and is capable of at least endothelial and hematopoietic differentiation.

It is contemplated that Matrigel®, laminin, collagen (especially collagen type I), fibronectin and glycosaminoglycans may all be suitable as an extracellular matrix, by themselves or in various combinations.

The invention will be more fully understood upon consideration of the following non-limiting Examples.

EXAMPLES

Example 1: Generation of MSCs from Pluripotent Stem Cells Under Serum-Free Conditions hESCs (H1; WiCell; Madison, Wis.) were maintained on irradiated mouse embryonic fibroblasts in a serum-free medium, such as DMEM/F12 medium supplemented with 20% Knockout™ serum replacer, 2 mM L-glutamine, 1× (100 µM) non-essential amino acids, 100 µM 2-mercaptoethanol and 4 ng/ml bFGF (all from Gibco-Invitrogen; Carlsbad, Calif.). See Amit M, et al., "Clonally derived human embryonic stem cell lines maintain pluripotency and proliferative potential for prolonged periods of culture," Dev. Biol. 227:271-278 (2000), incorporated herein by reference as if set forth in its entirety. Mouse OP9 bone marrow stromal cells (kindly provided by Dr. Toru Nakano and available from ATCC, catalog #CRL-2749) were maintained by four-day subculture on gelatin-coated dishes in alpha MEM medium (Gibco-Invitrogen) with 20% fetal calf serum (FCS; HyClone; Logan, Utah).

The hESCs were induced to differentiate by co-culture with mouse OP9 bone marrow stromal cells, as previously described. Vodyanik M, et al., "Human embryonic stem cell-derived CD34+ cells: efficient production in the coculture with OP9 stromal cells and analysis of lymphohematopoietic potential," Blood 105:617-626 (2005), incorporated herein by reference as if set forth in its entirety. Briefly, small aggregates of hESCs were added to OP9 cells in alpha MEM supplemented with 10% FCS and 100 µM MTG (Sigma; St. Louis, Mo.). On the next day (day 1) of culture, the medium was changed, and the cultures were harvested on the days indicated below.

On day two of hESC (H1) co-culture with OP9 stromal cells, peak expression of transcription factors for primitive streak population (mesendoderm) (GSC, EOMES, MIXL1 and T (BRACHYURY)) and early mesoderm (EVX1, LHX1 and TBX6) were detected with NimbleGen® (Madison, Wis.) microarrays.

On days 3-5 of co-culture, the culture contained mesenchymal progenitors, as well as cells expressing genes characteristic of endoderm and mesoderm. Among the genes characteristic for mesoderm, only genes characteristic of the lateral plate mesoderm, such as FOXF1, HAND1, NKX2-5, and GATA2 were expressed consistently. In contrast, genes characteristic for the axial (CHRD, SHH), paraxial (MEOX1, TCF15), or intermediate (PAX2, PAX8) mesoderm were not expressed consistently. Thus, hESCs co-cultured with OP9 cells for 3-5 days gave rise to cells expressing genes characteristic of the lateral plate/extraembryonic mesoderm. On days 3-5 of hESC(H1)/OP9 co-culture, the cells were also characterized by maximal cell proliferation and sustained expression of genes involved in epithelial-mesenchymal transition (EMT, SNAI1, and SNAI2) and cell expansion (HOXB2, HOXB3).

On days 5-7 of hESC(H1)/OP9 co-culture, differentiation into specific mesodermal and endodermal lineages was observed, when markers of developing endoderm (AFP and SERPINA1), mesenchymal (SOX9, RUNX2, and PPARG2), and hematoendothelial (CDH5 and GATA1) cells were detected. Neither muscle-inductive factors (MYOD1, MYF5, and MYF6) nor neuroectoderm (SOX1, PAX6, and NEFL) or trophectoderm (CGB and PLAC) markers were expressed throughout the seven days of co-culture, indicating that OP9 cells provided an efficient inductive environment for directed hESC differentiation toward the mesendodermal pathway.

On day 2 of hESC(H1)/OP9 co-culture, a single-cell suspension was harvested from the co-culture by successive enzymatic treatment with collagenase IV (Gibco-Invitrogen) at 1 mg/ml in DMEM/F12 medium for 15 minutes at 37° C. and 0.05% Trypsin-0.5 mM EDTA (Gibco-Invitrogen) for 10 minutes at 37° C., Cells were washed 3 times with PBS-5% FBS, filtered through 70 µM and 30 µM cell strainers (BD Labware; Bedford, Mass.) and labeled with anti-mouse CD29-PE (AbD Serotec; Raleigh, N.C.) and anti-PE paramagnetic monoclonal antibodies (Miltenyi Biotec; Auburn, Calif.). The cell suspension was purified with magnet-activated cell sorting (MACS) by passing it through a LD magnetic column attached to a Midi-MACS separation unit (Miltenyi Biotech) to obtain a negative fraction of OP9-depleted, hESC-derived cells. Purity was verified using pan anti-human TRA-1-85 monoclonal antibodies (R&D Systems; Minneapolis, Minn.).

The purified single-cell suspension was plated at density of 0.5-2×10$^4$ cells/ml on a semisolid, serum-free medium composed of StemLine™ serum-free medium (Sigma; St. Louis, Mo.) supplemented with 5-100 ng/ml bFGF (PeproTech; Rocky Hill, N.J.) and 1% methylcellulose (Stem Cell Technologies; Vancouver, Canada) with or without 10-20 ng/ml PDGF-BB (PeproTech). PDGF-BB improved growth of mesenchymal cells, but was not essential for colony formation. Alternatively, single cell suspensions were plated in a semisolid colony-forming serum-free medium containing 40% ES-Cult M3120 methylcellulose, 25% serum-free expansion medium (SFEM, Stem Cell Technologies), 25% endothelial serum-free medium (E-SFM, Invotrogen), 10%

BIT 9500 (Stem Cell Technologies), GlutaMAX (diluted 1:100), Ex-Cyte (diluted 1:1000, Millipore), 100 µM monothioglycerol (MTG), 50 µg/ml ascorbic acid and 20 ng/ml bFGF.

After 10-20 days of culture, large, compact mesenchymal colonies formed that resembled embryoid bodies (EBs). While these mesenchymal colonies were detected as early as day 7, 10-20 days of culture were required to reveal actively growing colonies. Undifferentiated hESCs or cells harvested on day 1 or on day 6 of co-culture did not form these mesenchymal colonies when cultured under the same conditions.

Mesenchymal colonies, which resembled embryoid-like bodies, were distinguished from EBs through several characteristics: (1) formation and growth under serum-free conditions supplemented with bFGF and stimulation by factors promoting mesenchymal cell growth (e.g., PDGF-BB, EGF and TGF-α), but suppression by factors involved in mesodermal differentiation (e.g., VEGF, TGF-β and Activin A) in mesenchymal colonies; (2) lack of a dense outer cell layer and irregular cavitated structure characteristic of EBs, even after prolonged culture in mesenchymal colonies; (3) presence of morphological homogeneity in cells comprising the mesenchymal colonies; and (4) formation of colonies through establishment of tightly packed structures (cores) which further develop into compact spheroid colonies.

To demonstrate that the single-cell suspensions did not form aggregates upon plating in semi-solid medium, clonality of the mesenchymal colonies obtained in the culture methods was tested and confirmed using chimeric hESC lines established from cells retrovirally marked with a reporter gene, e.g., either enhanced green fluorescent protein (EGFP) or histone 2B-(H2BB) mOrange fluorescent protein. Expression of a product of the reporter gene indicated clonality. The chimeric hESC lines were generated from two lentiviral constructs: (1) the EGFP protein expressed constitutively from an elongation factor 1 alpha (EF1alpha) promoter, and (2) the H2BB-mOrange protein expressed constitutively from the EF1alpha promoter. Both constructs were packaged in 293FT cells, and the lentiviruses were used to transduce H1 hESCs to produce stable H1 hESC lines that expressed either green EGFP protein or orange H2BB-mOrange protein. Mesenchymal colonies derived from the described methods were of single colors, either green or orange, thus indicating the clonal (i.e., single cell) origin of the MSCs. In addition, prospective phenotypic analysis demonstrated a positive correlation between mesenchymal-colony forming cell (CFC) frequency and KDR (VEGFR2) expression, though KDR$^{high}$CD34+ population of the earliest hemangiogenic precursors was devoid of mesenchymal-CFCs. Analysis of cells within mesenchymal colonies revealed a homogeneous population of early mesenchymal cells defined by high, CD90, CD140a and CD166 expression, low CD44, CD56 and CD105 expression and lack of CD24, CD31, CD43, CD45, CD144 (VE-cadherin), and lack of SSEA4 expression. In addition, mesenchymal colonies expressed vimentin, alpha smooth muscle actin, and desmin. Furthermore, mesenchymal colonies expressed genes specific for MSC lineage, such as FOXF1, MSX1, MSX2, SNAI1, SNAI2, SOX9, and RUNX2.

Individual mesenchymal colonies were transferred to wells of a collagen- or fibronectin-coated, 96-well plate pre-filled with 0.2 ml/well StemLine™ serum-free medium supplemented with 5-100 ng/ml bFGF or serum-free expansion medium consisting of 50% StemLine II serum-free HSC expansion medium (H-SFEM, Sigma), and 50% E-SFM supplemented with GlutaMAX (diluted 1:100), ExCyte (diluted 1:2000), 100 µM MTG, and 10 ng/ml bFGF. After 3-4 days of culture, adherent cells from individual wells were harvested by trypsin treatment and expanded on collagen- or fibronectin-coated dishes in StemLine™ serum-free medium with 5-100 ng/ml bFGF or serum-free expansion medium (M-SFEM) containing 50% StemLine™ II serum-free HSC expansion medium (HSFEM; Sigma), 50% E-SFM, GlutaMAX™ (1/100 dilution), Ex-Cyte® supplement (1/2000 dilution), 100 µM MTG, and 5-100 ng of bFGF.

MSCs were expanded for many passages. When individual colonies were plated on collagen- or fibronectin-coated plates, immediate attachment and vigorous outgrowth of fibroblast-like cells were observed. During subsequent passages, cells grew intensively during the first 10 passages; however, growth rate was attenuated at passages 10-15 and gradual senescence was observed during passages 15-20. Cultures derived from single MB-CFC accumulated up to $10^{22}$ total cells in the observed time period. Because each colony is presumed to have originated from a single cell, the number corresponds to the expansion potential of a single hESC-derived mesenchymal precursor.

Cell lines established from individual colonies were maintained in serum-free medium with bFGF for 10-15 passages at a high proliferation rate. All cell lines displayed a mesenchymal phenotype, characterized by expression of CD44, CD56, CD 73, CD105, CD146, and CD140a (PDGFRA) and lack of hematoendothelial markers (i.e. CD31, CD43, CD45 and VE-cadherin). When tested in conditions revealing mesenchymal differentiation potential, the cell lines were capable of osteogenic, chondrogenic and adipogenic differentiation. Interestingly, these cells resemble bone marrow MSCs, but expand and proliferate better than bone marrow MSCs. These expanded mesenchymal cells could be differentiated into cells of the chondro-, osteo- and adipogenic lineage. However, these cells could not give rise to hematopoietic or endothelial cells when cultured with OP9 cells, or when cultured in feeder-free cultures with hematoendothelial growth factors (VEGF, bFGF, SCF, TPO, IL3, IL6), indicating a limited differentiation potential of these mesenchymal cells.

Mesenchymal colonies were also generated from various induced pluripotent stem (iPS) cells, such as iPS(IMR90)-1, iPS(SK)-46, and iPS(FSK)-1 reprogrammed using a lentiviral vector (Yu et al., Science 318:1917-1920 (2007)), or transgene-free iPS-5 4-3-7T and iPS-1 19-9-7T (Yu et al., Science 324:797-801 (2009)). Mesenchymal colonies derived from transgene-containing iPS cells displayed irregular or more loose morphology. Transgene-free iPSC produced typical spheroid mesenchymal colonies.

Example 2. In Vitro Generation and Characterization of Mesangioblasts

To isolate and characterize a population of mesodermal progenitors that can give rise to cells of the mesodermal lineage with hematopoietic, endothelial, and mesenchymal stem cell potentials, H1 hES cells were co-cultured with OP9 cells, as described in Example 1. After two or three days of co-culture, when genes representative of primitive streak population (mesendoderm) (MIXL1, T, EOMES) were expressed, the hESC-derived cells depleted of OP9 cells using anti-mouse CD29 antibody were plated in semi-solid, serum-free medium, essentially as described in Example 1, with 20 ng/ml bFGF (PeproTech; Rocky Hill, N.J.). The number of colony-forming cells (CFCs) was calculated per 1000 plated H1-derived TRA-1-85$^+$ cells.

Figures 1B, 1C:
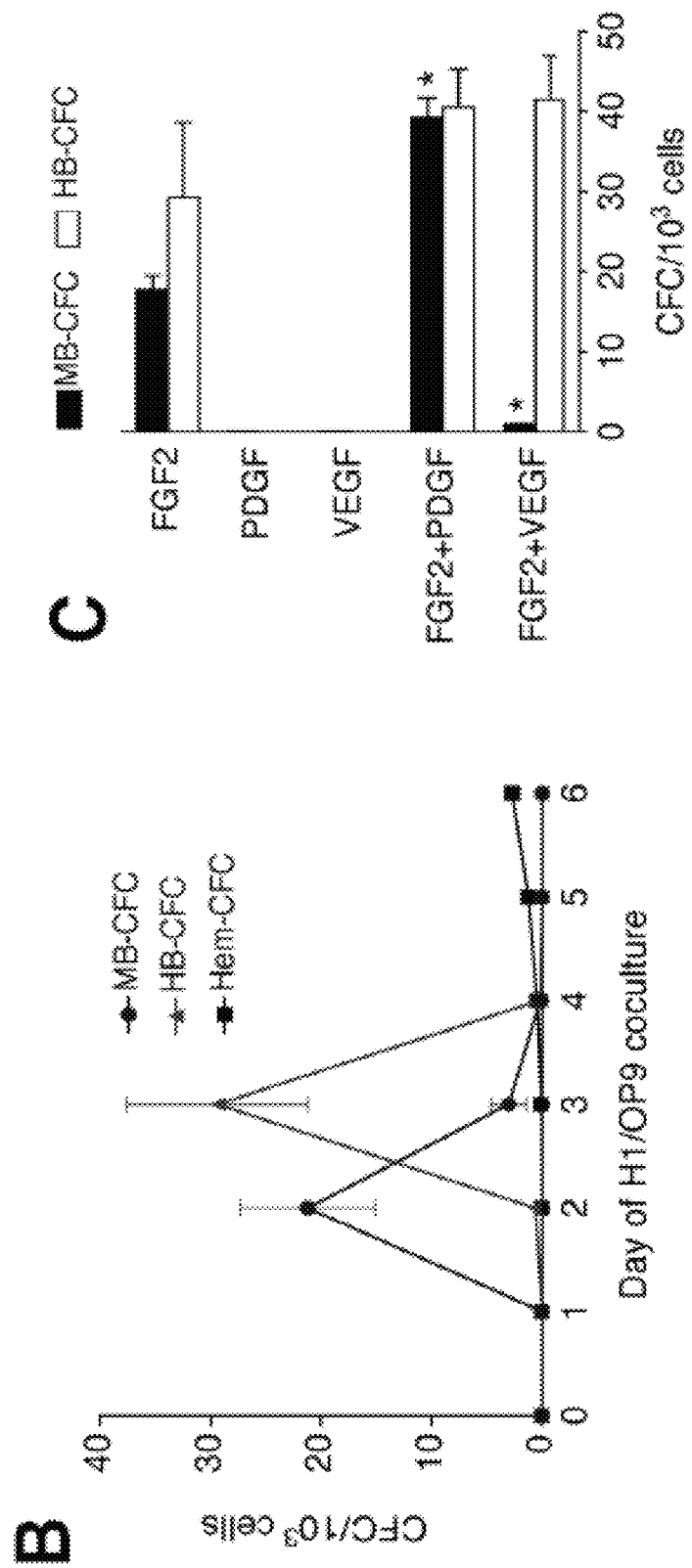

After 2-3 days in semisolid medium, the cells formed tightly packed structures (cores). Cores derived from hESCs that were differentiated in co-culture with OP9 cells for 2 days further grew into spheroid mesenchymal colonies. Cores derived from hESCs that were differentiated in co-culture with OP9 cells for 3 days further grew into dispersed blast colonies with hematopoietic and endothelial potential.

bFGF is necessary and sufficient for the formation of both colonies from hESCs. bFGF supported both mesenchymal and blast colony formation. In contrast, in the absence of bFGF, neither VEGF, nor PDGF-BB (FIG. 1A), SCF, IGF1, or HGF (data not shown), alone or in combination, supported formation of either colony. While PDGF-BB (10 ng/ml) alone did not support colony formation, PDGF-BB in combination with bFGF significantly increased the yield and size of mesenchymal colonies compared to bFGF alone (FIG. 1A). VEGF alone (20 ng/ml) did not support colony formation but its addition to bFGF cultures slightly increased the number of blast colonies, but inhibited formation of mesenchymal colonies (FIG. 1A). Cells that gave rise to each colony type constituted approximately 2-3% of total hESC-derived cells (FIG. 1B).

To determine if cells within the mesenchymal colonies can give rise to cells of the hematovascular lineage, individual mesenchymal colonies were picked from the methylcellulose on day 5-7 and plated onto OP9 cells in alpha-MEM medium with 10% FBS, and the cytokines SCF (50 ng/ml), TPO (50 ng/ml), IL-3 (10 ng/ml), and IL-6 (20 ng/ml). After 4 days of culture, cells were harvested and analyzed by flow cytometry or stained in situ with rabbit anti-human CD144 (VE-cadherin; 1 µg/ml; eBioscience, San Diego, Calif.) in combination with mouse anti-human CD43 (0.5 µg/ml; BD Bioscience) or mouse anti-human Calponin (0.5 µg/ml; Thermo Fisher Scientific) primary antibodies, followed by a mixture of secondary cross-absorbed donkey anti-mouse IgG-DyLight 594 and donkey anti-rabbit IgG-DyLight-488 (both at 2 µg/ml; Jackson ImmunoResearch Laboratories, Inc., West Grove, Pa.) antibodies.

Figure 1D:
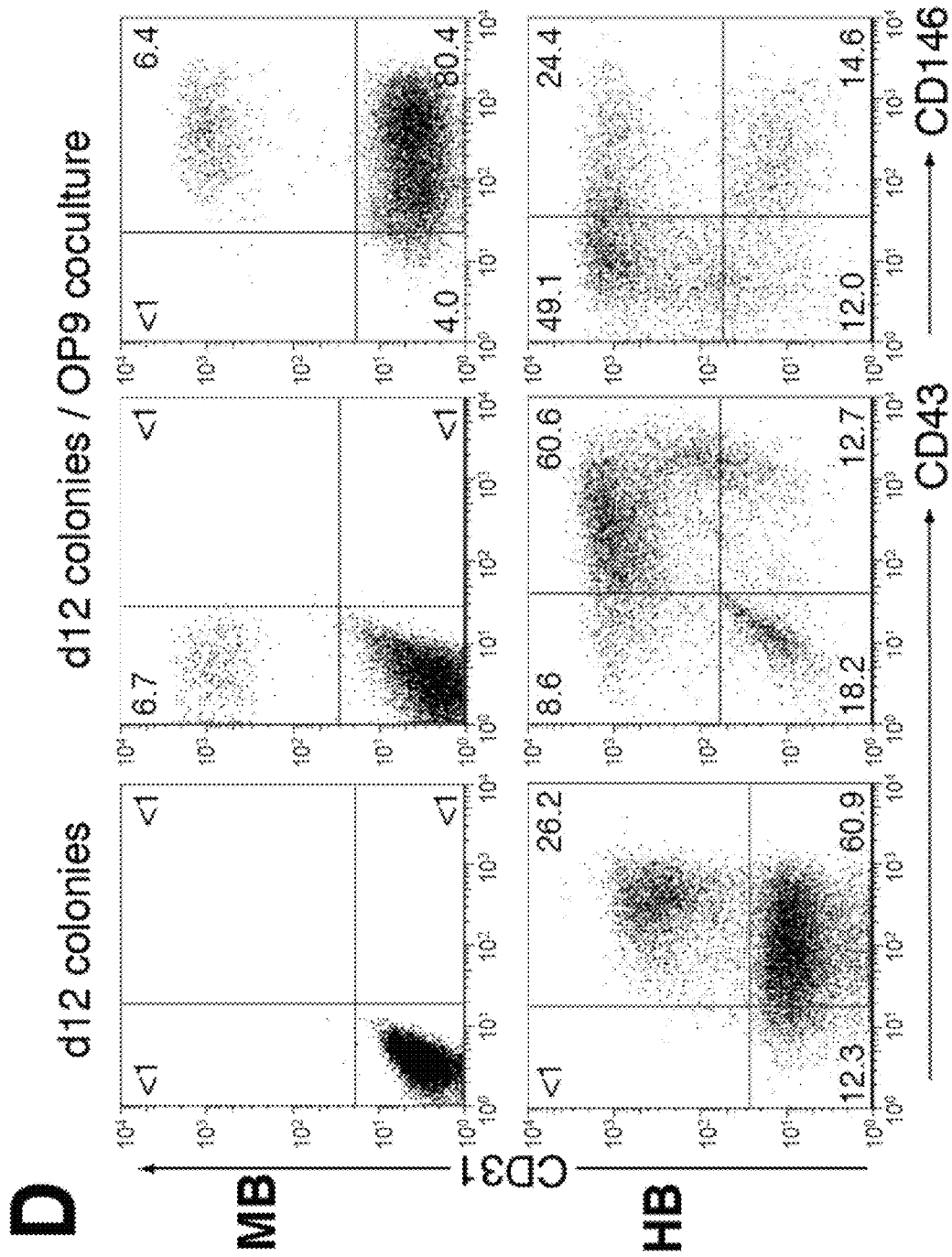
Figure 1E:
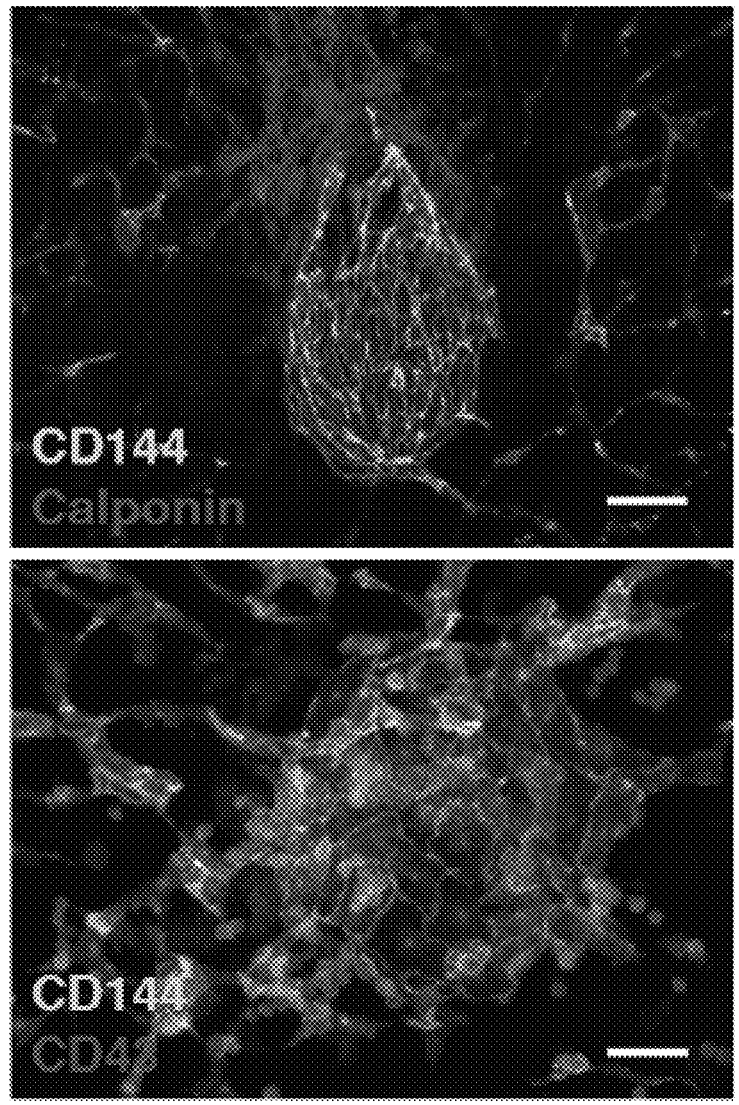
Figure 2A:
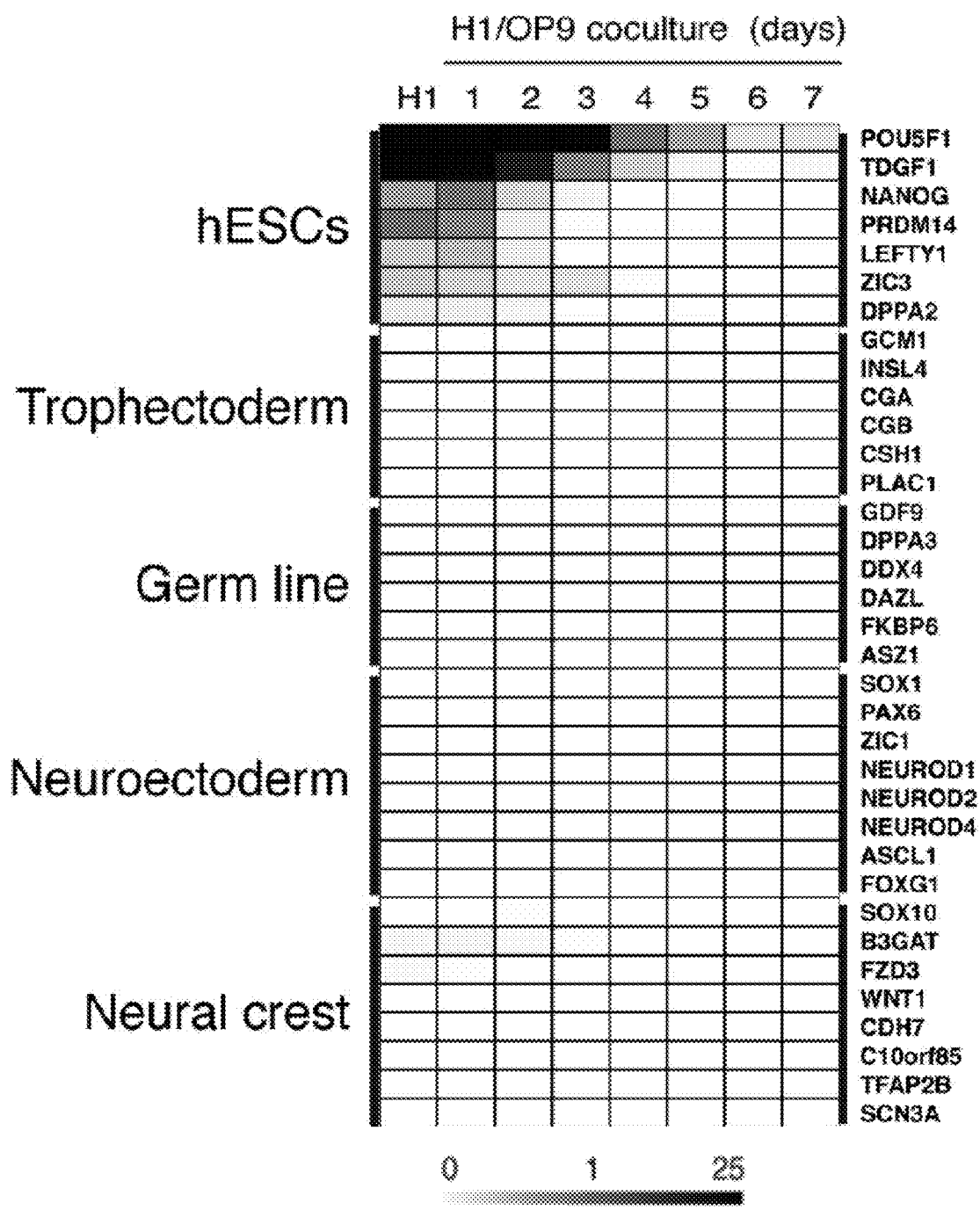
FIG. 2A depicts a heat map for selected gene sets defining particular germ layers and their subpopulations and derivatives.
Figure 2A:
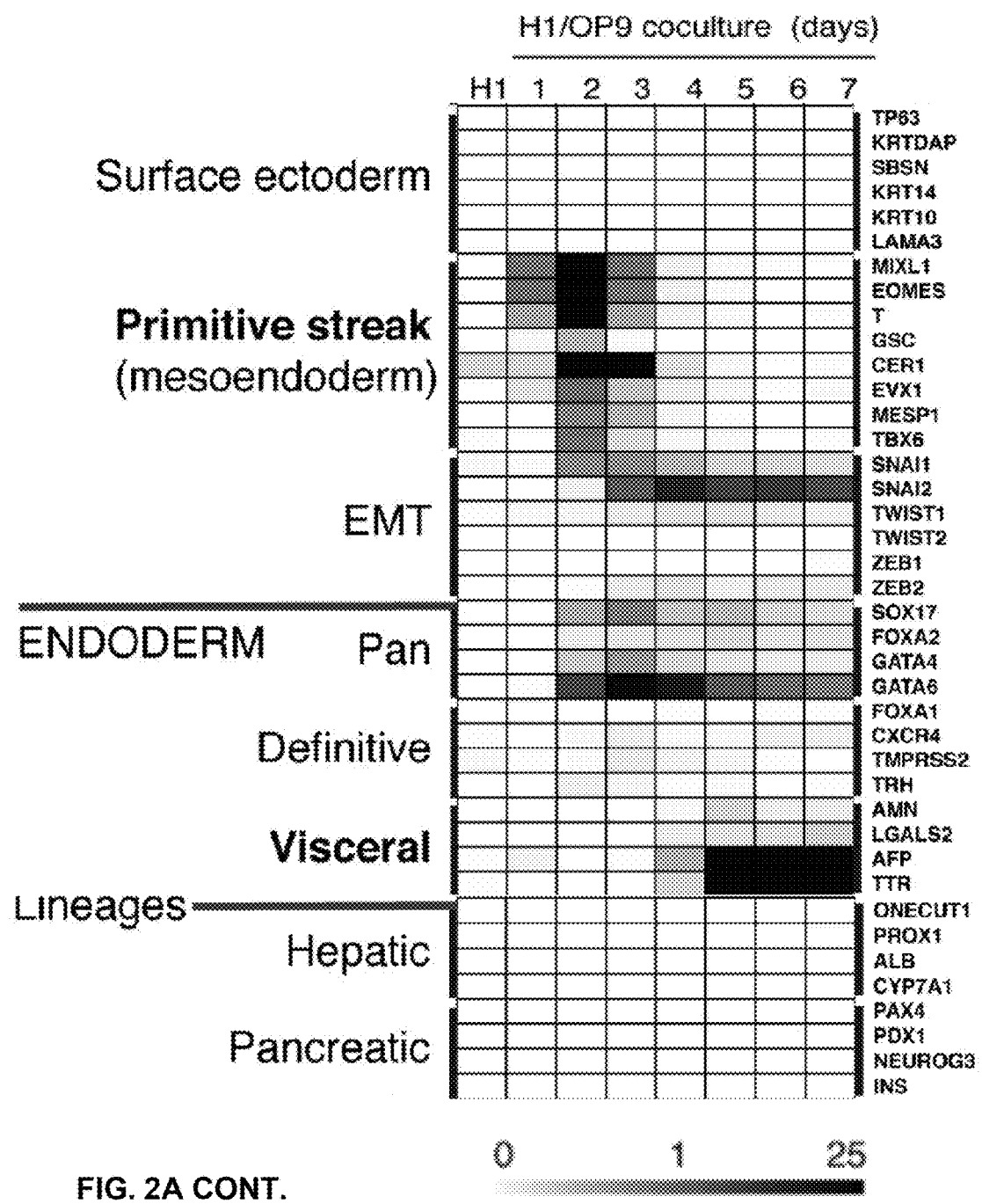
Figure 2A:
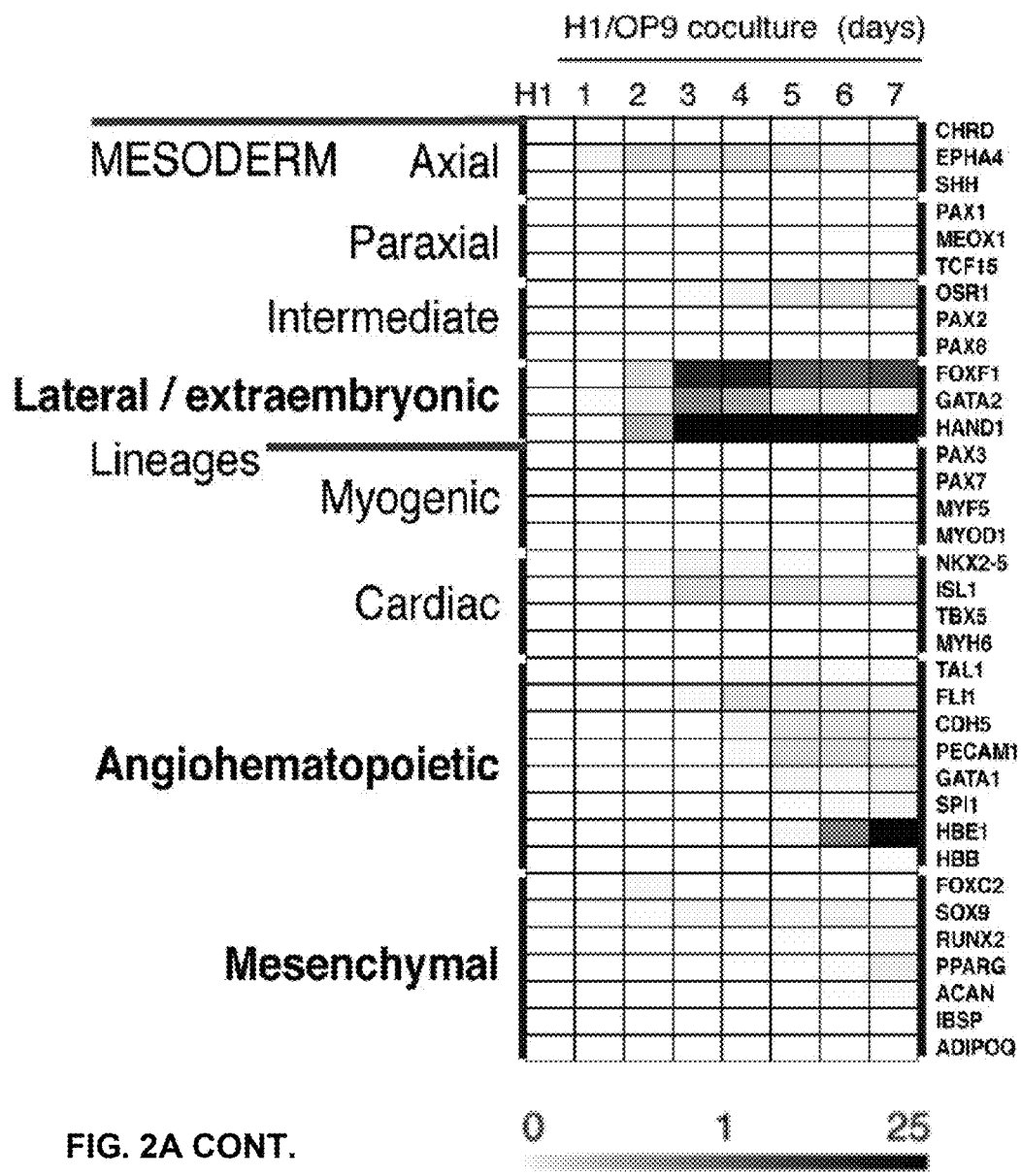
Figure 2B:
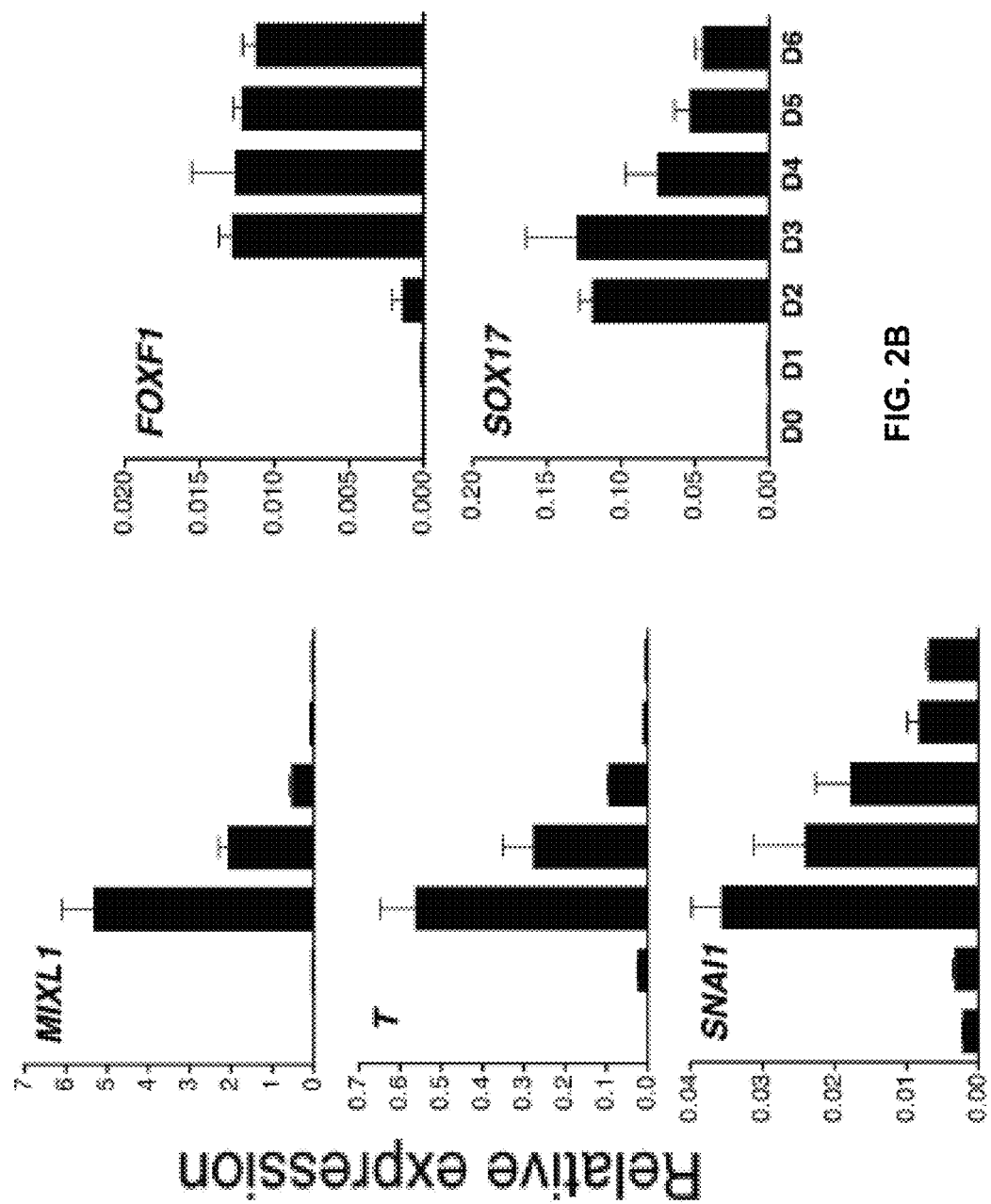
FIG. 2B depicts relative gene expression of MIXL1, T, SNAI1, FOXF1, and SOX17 as determined by quantitative PCR.
Figure 2C:
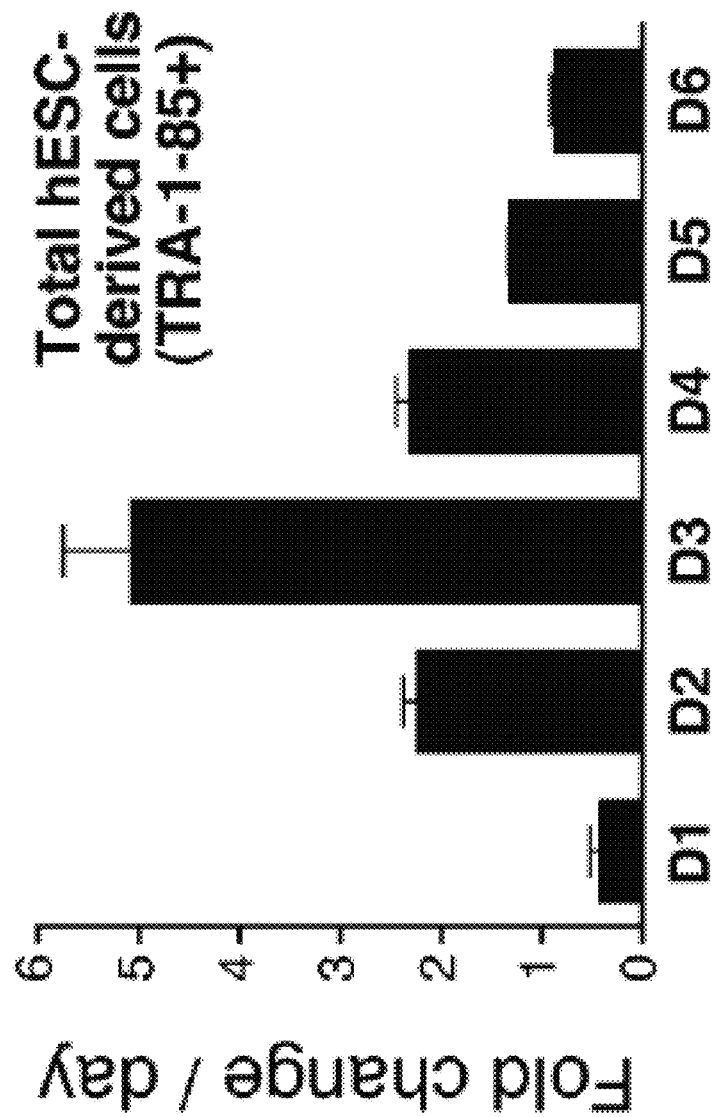
FIG. 2C depicts the fold increase in the number of hESC-derived cells after day 1-6 of OP9 co-culture in relation to previous day. The data is represented as means±SD (n=3).

The mesenchymal colonies originated from precursors that gave rise to endothelial and mesenchymal cells, i.e. mesangioblasts. As explained in Example 1, MSCs expanded from mesenchymal colonies in adherent cultures did not give rise to hematopoietic or endothelial cells when cocultured with OP9 cells. In contrast, approximately 70% of mesenchymal colonies isolated from day 5-7 colony-forming cultures in semisolid media gave rise to CD31$^+$CD144(VE-cadherin)$^+$ endothelial cells when cocultured with OP9 cells. (FIGS. 1D and E, upper panels). The mesenchymal colonies, therefore, originated from common precursors for endothelial and mesenchymal lineages, i.e., mesangioblasts. In contrast, blast colonies contained CD31$^+$CD43$^+$ hematopoietic cells and could give rise to endothelial cells (FIGS. 1D and E lower panels).

The endothelial potential of mesenchymal colonies could be significantly enhanced with the addition of bone morphogenic protein 4 (BMP4) to the clonogenic assay medium (3.2±2.4% CD31$^+$CD43$^-$ cells without BMP4 vs. 11.6±0.5 with 5 ng/ml BMP4).

Example 3: Generating and Isolating a Population of Cells Substantially Enriched in Lateral Plate/Extraembryonic Mesoderm Cells Genetic profiling of H1 hESCs differentiated in OP9 cocultures demonstrated selective commitment toward mesodermal and endodermal lineages with no detectable ectoderm (tropho-, neuro-, or surface ectoderm) (FIG. 2). The cells became committed to mesendoderm by day 2 of culture, when synchronous expression of primitive streak genes (MIXL1, T, and EOMES) was detected. At subsequent days of culture, mesoderm- and endoderm-specific genes and, eventually, endoderm- and mesoderm derivative-specific genes were expressed. Of the mesodermal genes, those characteristic of the lateral plate/extraembryonic mesodermal subset (FOXF1, HAND1, NKX2-5, GATA2) were expressed consistently, while expression of genes of the axial (CHRD, SHH), paraxial (MEOX1, TCF15), or intermediate (PAX2, PAX8) subsets was not consistent. Apelin receptor (APLNR) expression is strongly induced and up-regulated on days 2-3 of differentiation, concurrently with mesodermal commitment.

Figure 3A:
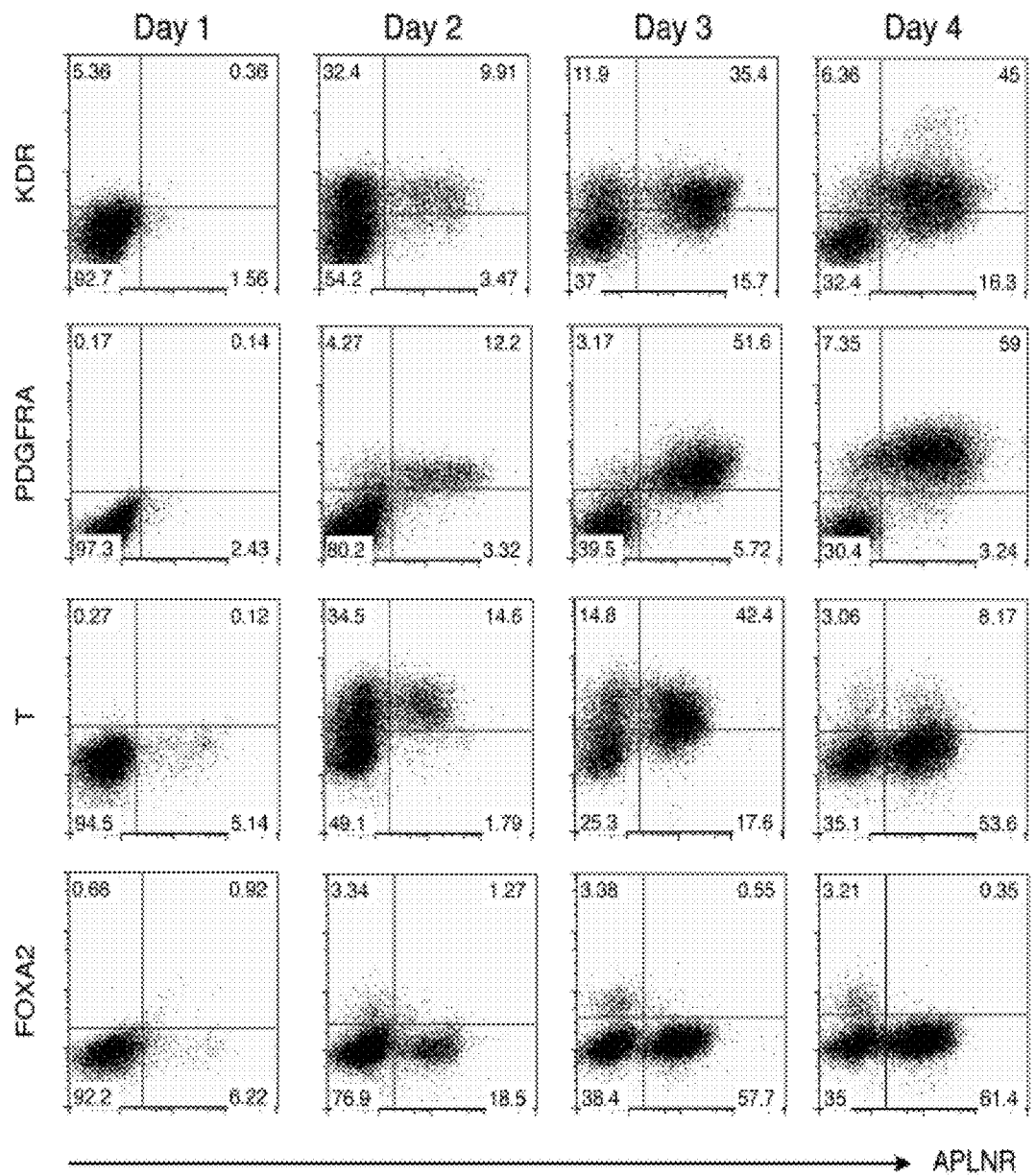
FIG. 3A depicts dot plots of flow cytometry results.
Figure 3B:
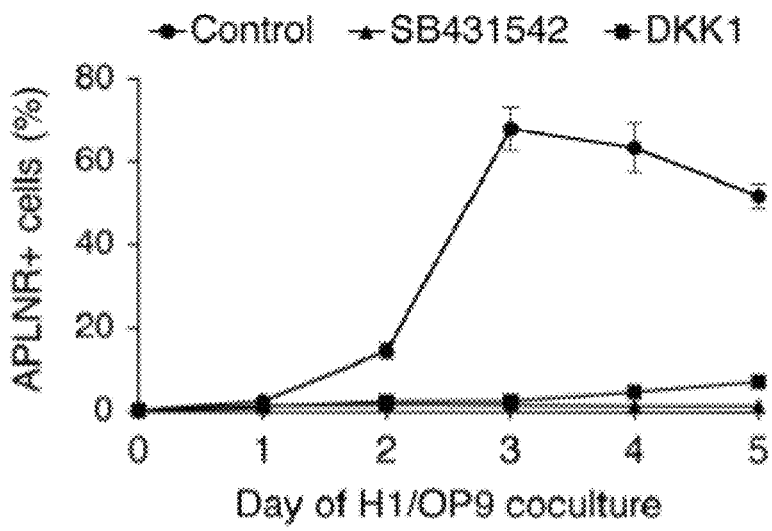
FIG. 3B depicts the effect of inhibitors of mesoderm formation (SB431542 (5 µg/ml) and DKK1 (150 µg/ml)) on generation of APLNR+ cells from H1 cells in OP9 cell co-cultures.

To characterize APLNR expression and the cells that express it, hESCs differentiated in OP9 co-cultures were stained with monoclonal antibodies specific for Apelin receptor (APLNR) (R&D Systems) in combination with antibodies against CD30, KDR, PDGFRA, T, and FOXA2. Undifferentiated hESCs and hESC-derived cells on day 1 of OP9 co-culture were APLNR negative (FIG. 3A, Day 1 panels). Expression of APLNR was strongly up-regulated in cells co-cultured with OP9 cells for 2-3 days (FIG. 3A, Day 2 and 3). On day 2, 15-20% of cells were APLNR$^+$ and by day 3, 60-70% of cells were APLNR$^+$. This upregulation coincided with mesodermal commitment, as evidenced by the upregulation of mesodermal markers, such as KDR (VEGFR2), T, and PDGFRA (FIG. 3A, Day 2 and 3 panels). The number of APLNR$^+$ cells gradually decreased on subsequent days (FIG. 3B). Conversely, hESC markers (e.g. CD30) were successively down-regulated.

While PDGFRA is expressed only at low levels in day 2 co-cultures, APLNR is expressed at high density as early as day 2 of co-culture allowing separation of APLNR positive from APLNR negative cells. On days 2, 2.5, and 3 of H1/OP9 cell co-culture, APLNR$^+$ and APLNR$^-$ cells were separated by magnetic sorting and gene expression was analyzed by microarray analysis.

Figure 4A:
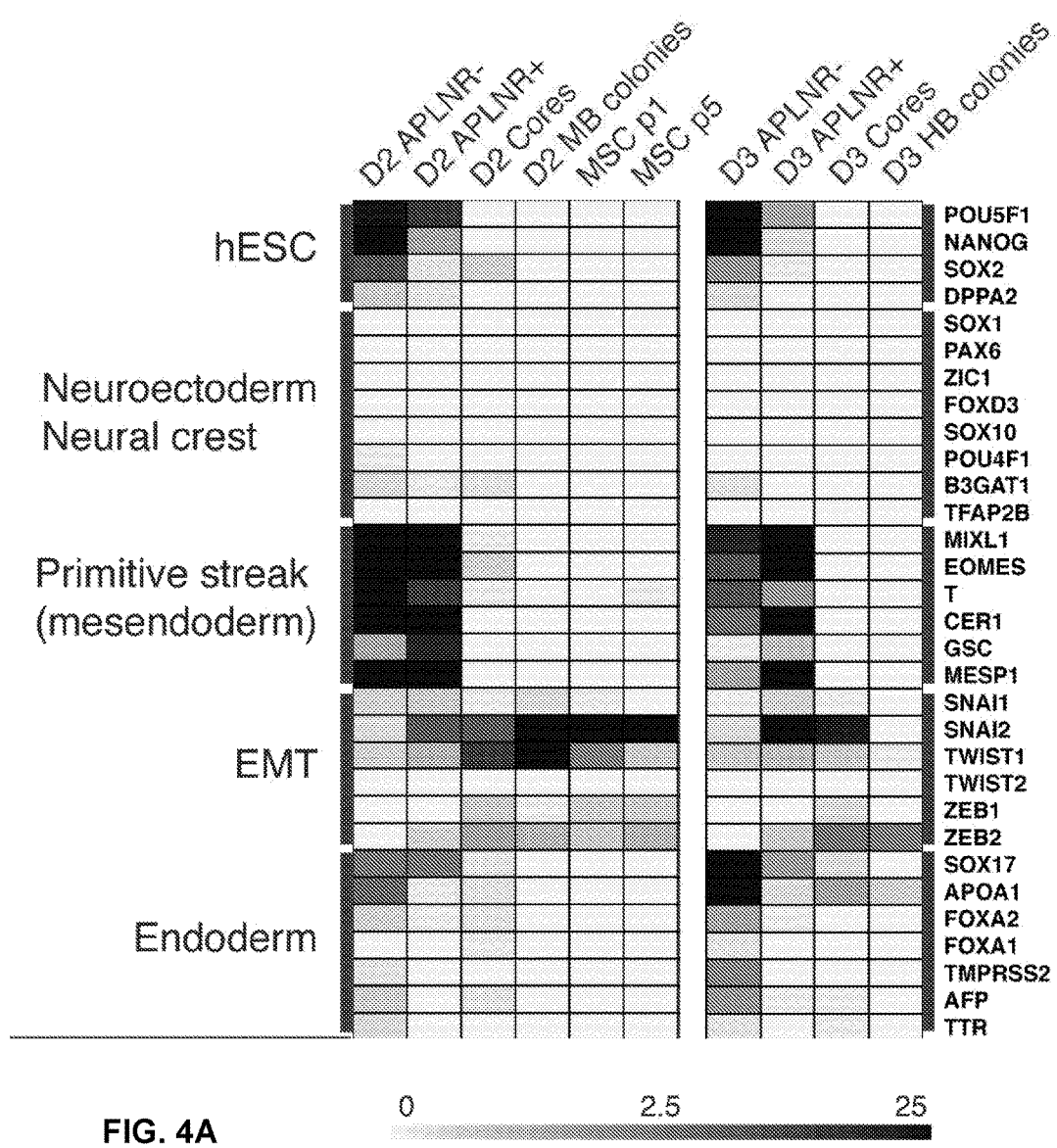
FIG. 4A depicts heat maps for selected sets of genes defining indicated germ layers and their subpopulations/derivatives. Cores were collected on day 3 of clonogenic cultures and fully developed colonies on day 12 of clonogenic cultures. EMT is epithelial-mesenchymal transition. VSMC is vascular smooth muscle cells.
Figure 4A:
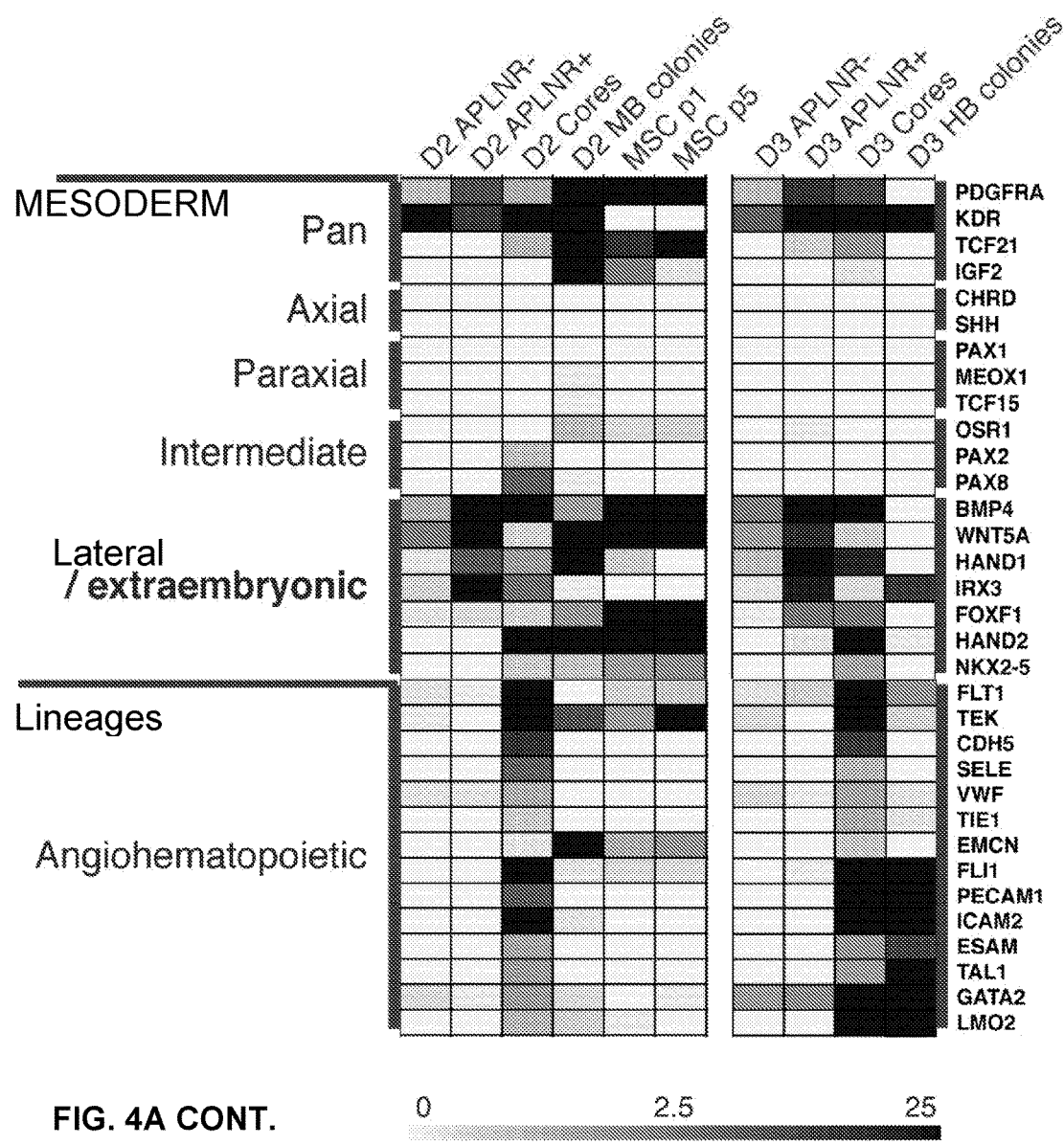
Figure 4A:
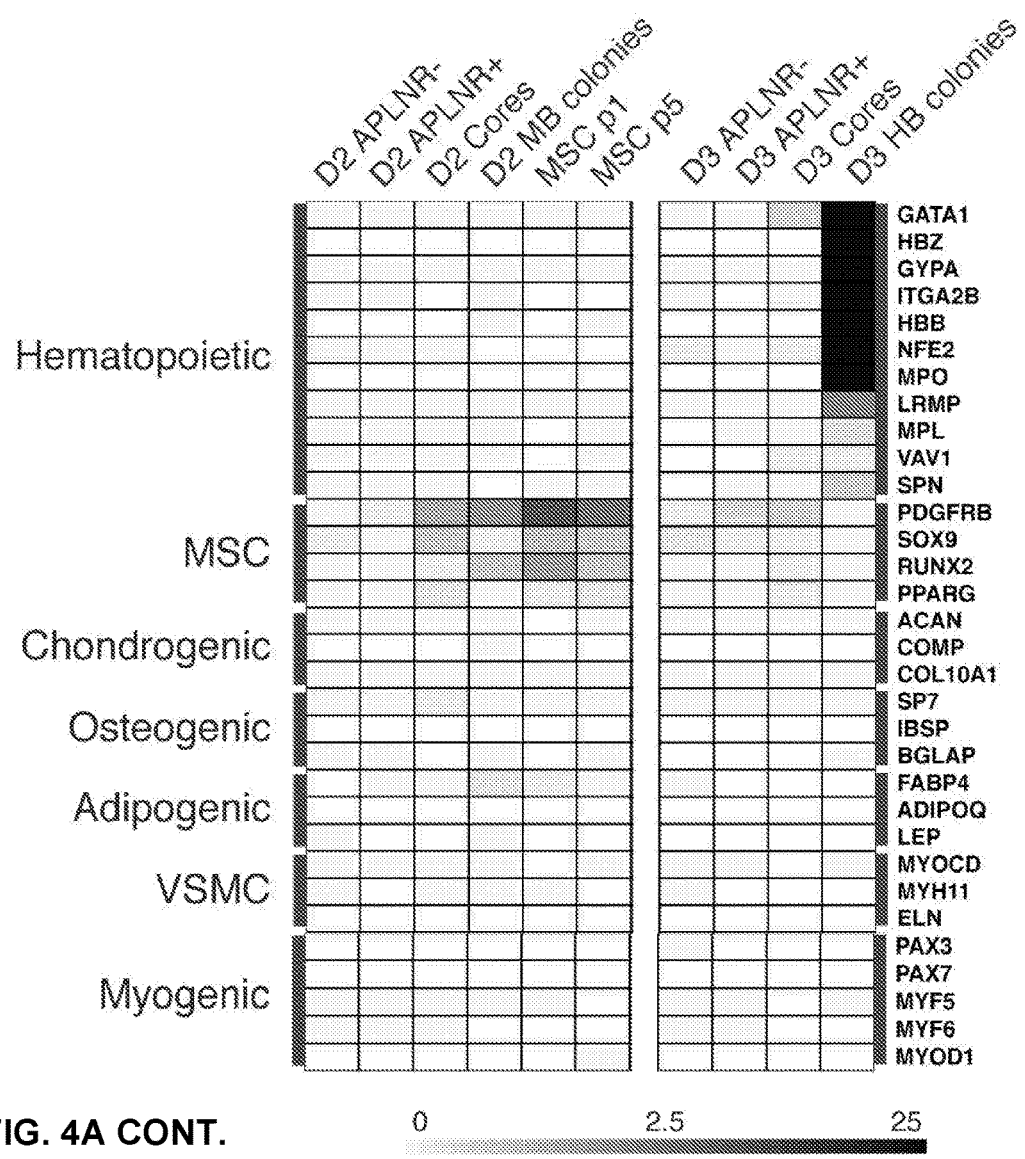
Figure 4B:
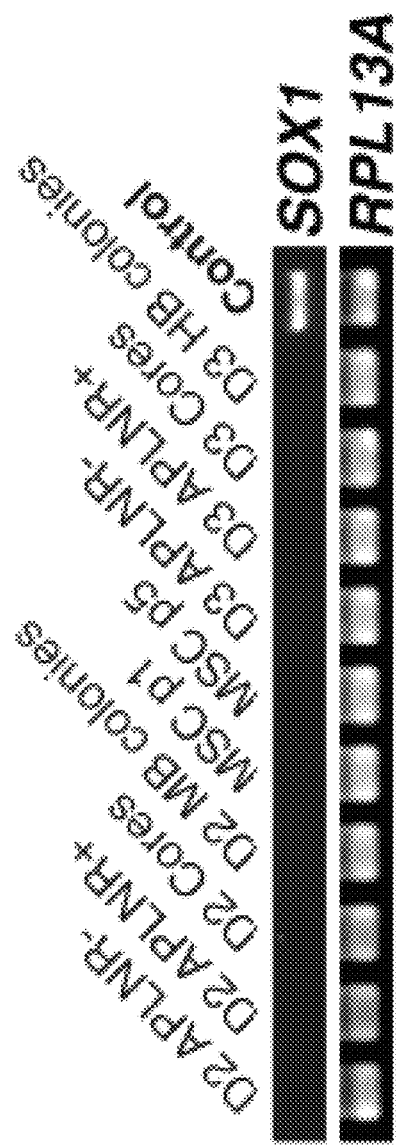
FIG. 4B shows lack of SOX1 neuroepithelium marker expression throughout all stages of differentiation. Embryoid bodies derived from H1 hESCs differentiated for 14 days were used as positive control.
Figure 4C:
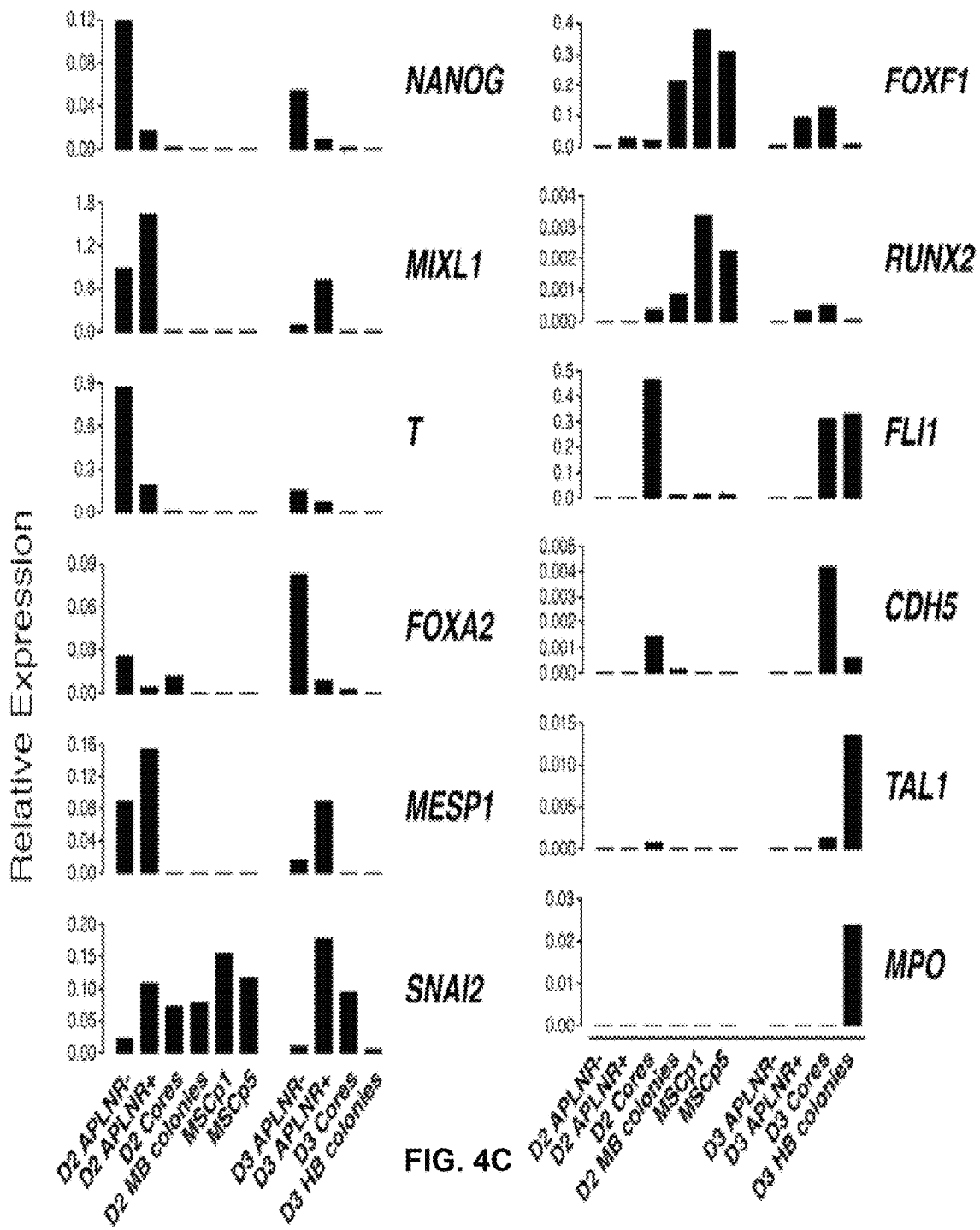
FIG. 4C illustrates quantitative RT-PCR analysis of representative transcripts in indicated cell subsets. Bars represent gene expression in pooled samples from 3 experiments normalized to RPL13.
Figure 5:
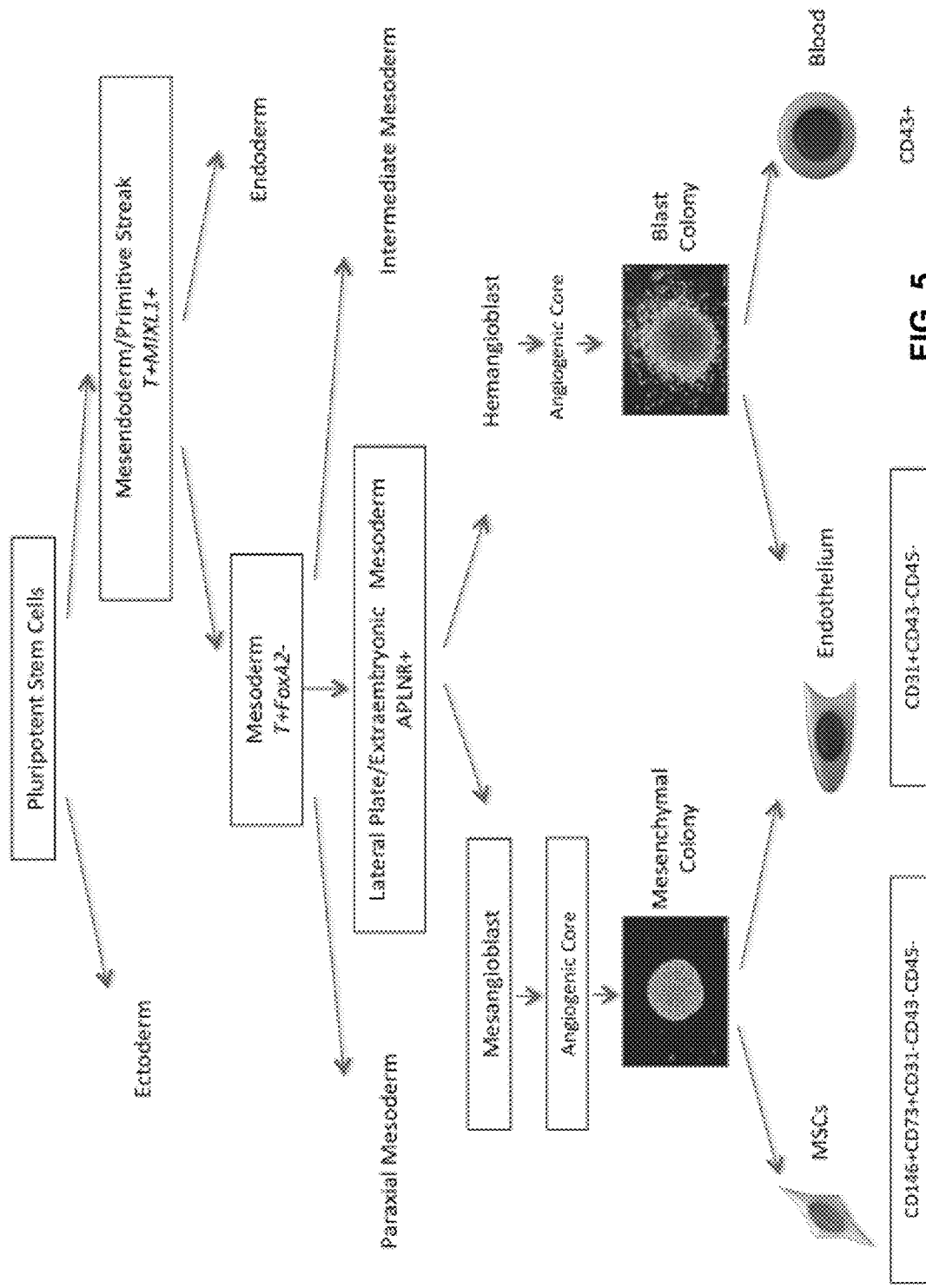
FIG. 5 depicts a schematic diagram of mesodermal lineages development and differentiation toward MSCs from pluripotent stem cells.
Figure 6:
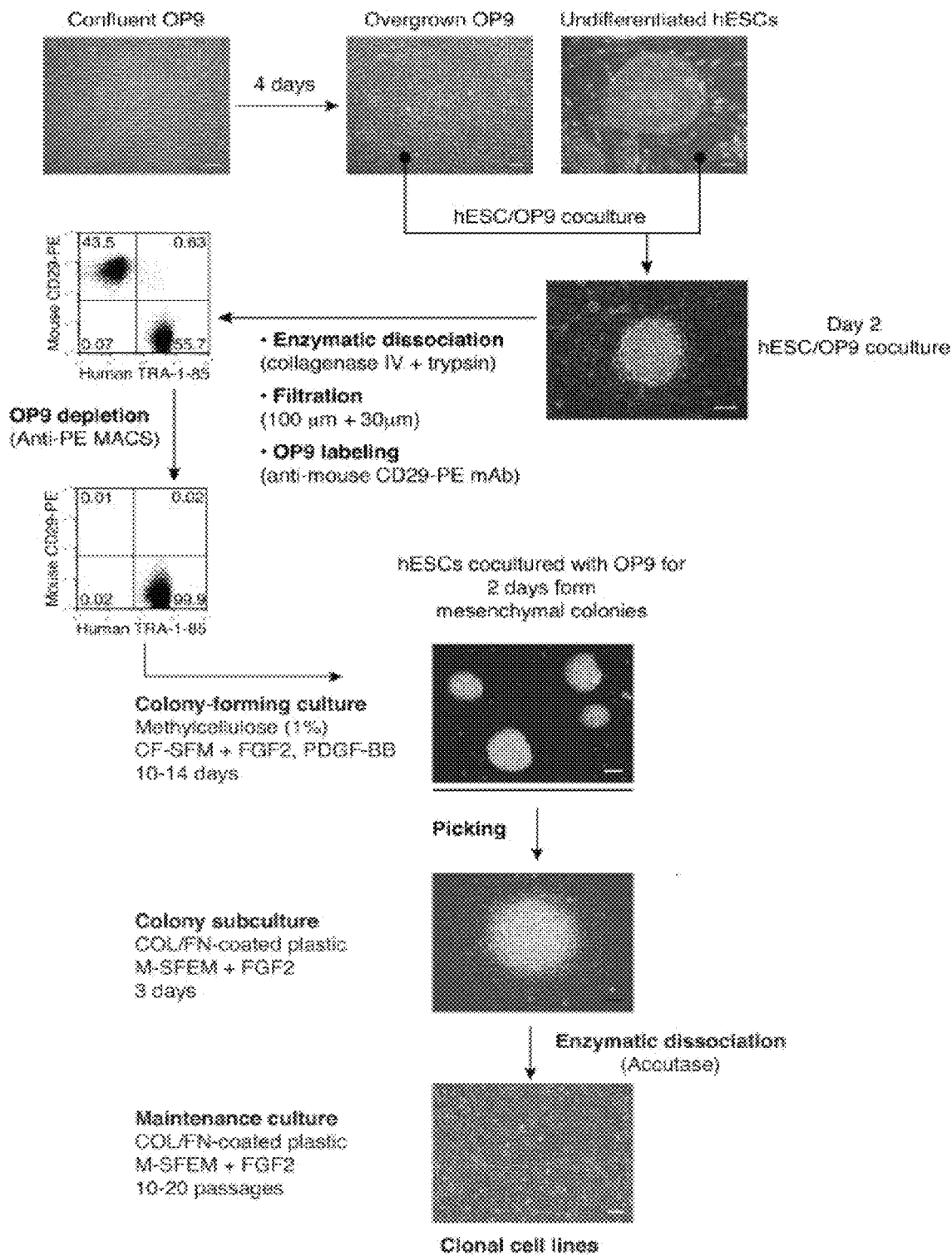
FIG. 6 depicts a schematic diagram of the protocol used for hESC differentiation, generation of MB colonies, and clonal MSC lines.
Figure 7:
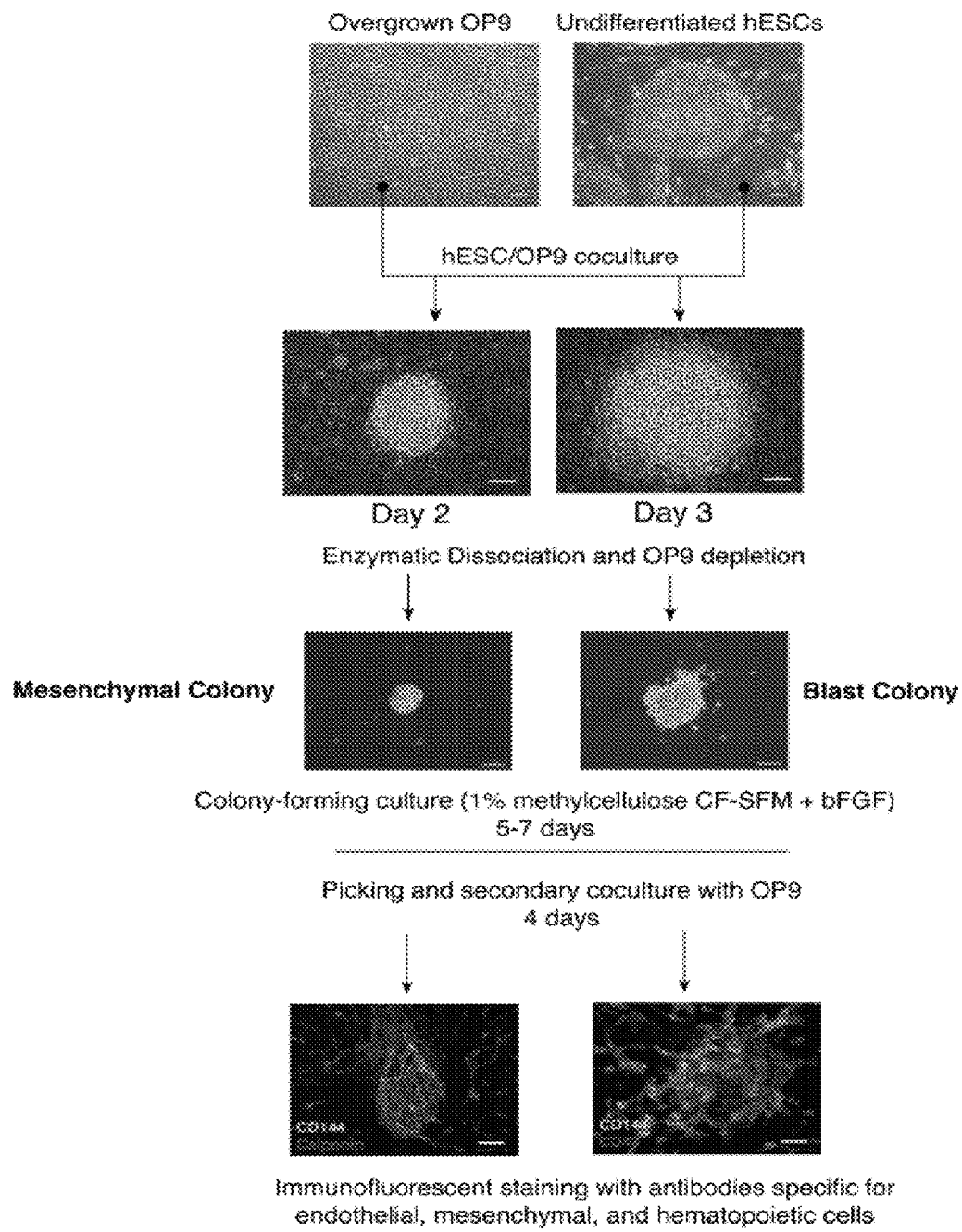
FIG. 7 depicts a schematic diagram of the protocol used to evaluate differentiation potential of mesenchymal and blast colonies.

MIXL1, T, and EOMES, indicative of primitive streak cells (mesendoderm), were all expressed in APLNR$^+$ cells, while transcripts associated with neural crest/neuroectoderm (POU4F1, SOX1, SOX2, SOX3, SOX10) could not be detected (FIGS. 4A and 4B). As expected, APLNR$^+$ cells were enriched in TCF21 mesoderm-specific transcripts, whereas transcripts marking pan-endoderm (FOXA2, APOA1), definitive (FOXA1, TMPRSS2), and visceral (TTR, AFP) endoderm were found in APLNR$^-$ cells (FIGS. 4A and C).

Figure 3C:
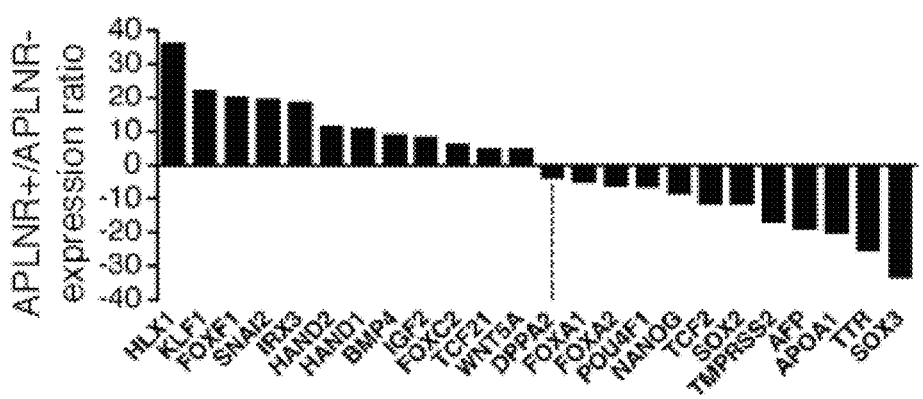
FIG. 3C compares transcript expression between APLNR+ and APLNR− cells.

Interestingly, APLNR$^+$ cells expressed FOXF1, IRX3, BMP4, WNT5A, NKX2.5, HAND1, and HAND2 representative of lateral plate/extraembryonic mesoderm, but not markers of paraxial/myogenic (MEOX1, TCF15, PAX3, PAX7) and intermediate (PAX2, PAX8) mesoderm in the embryo. This data indicates that rather than being a total population of cells committed to mesendodermal development, APLNR$^+$ cells represent mesoderm, or likely its subpopulation reminiscent of lateral plate/extraembryonic mesoderm (FIG. 3C and FIG. 4).

To further confirm mesodermal identity, APLNR$^+$ cells were analyzed for expression of T, a marker of early mesoderm, and FOXA2, a marker of endoderm. As shown in FIG. 3A, APLNR$^+$ cells are T$^+$ and maintain T expression until it subsides on day 4. In contrast, FOXA2$^+$ cells, which comprised less than 5% of total cells in culture, did not express APLNR. Thus, APLNR$^+$ cells are T$^+$FOXA2$^-$ mesodermal precursors on day 2-3 of culture.

To further support the notion that APLNR$^+$ cells are mesodermal precursors, H1/OP9 cell co-cultures were supplemented with inhibitors of mesoderm formation SB431542 (5 µg/ml) or DKK1 (150 µg/ml). APLNR$^+$ cells could not be detected in cultures that received the inhibitors of mesoderm formation (FIG. 3B), confirming that APLNR$^+$ cells are mesodermal. Further, mesenchymal and blast colony-forming potential was found exclusively within the APLNR$^+$ cell population (FIG. 3D), further confirming that both mesangiogenic mesenchymal and hemangiogenic blast colonies are formed by APLNR$^+$ mesodermal precursors.

Figure 3D:
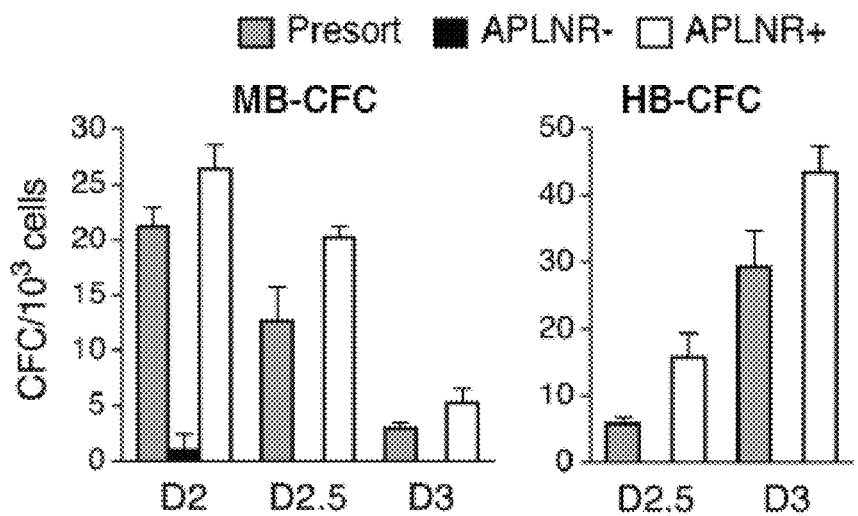
FIG. 3D depicts the colony-forming potential of APLNR+ and APLNR− cells.

Example 4. Enrichment of Mesangioblasts Derived from hESCs Under Serum-Free Conditions Through Isolation of APLNR$^+$ Lateral Plate/Extraembryonic Mesoderm Cells To identify the origin of mesenchymal colonies and obtain a population of cells enriched in mesangioblasts, pluripotent stem cells were co-cultured with OP9 for 2-3 days to induce mesoderm formation. After depletion of OP9 cells with mouse-specific CD29 antibodies, APLNR$^+$ and APLNR$^-$ cells were isolated using magnetic sorting. Colony formation assays in semisolid media in presence of bFGF demonstrated that mesangioblast and hemangioblast potential was confined solely to the APLNR$^+$ fraction (FIG. 3D). Approximately 1 to 5% of cells within APLNR$^+$ fraction possessed mesangioblast activity.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of generating primate cells expressing Apelin receptor (APLNR+), the method comprising the steps of:
   (i) co-culturing primate-embryonic stem (ES) or induced pluripotent stem (iPS) cells with OP9 bone marrow stromal cells for at least two to three days; and
   (ii) depleting OP9 bone marrow stromal cells from the cells obtained in step (i); and
   (iii) isolating cells expressing APLNR from cells obtained in step (ii) wherein a population of APLNR+ cells is produced.

2. The method of claim 1, wherein the method further comprises culturing the Apelin receptor positive (APLNR$^+$) cells obtained in step (iii) in semisolid media with bFGF, wherein about 1% to about 5% of the sorted APLNR$^+$ cells are capable of differentiating in culture into mesenchymal stem cells and endothelial cells.

3. A method of generating APLNR+ primate cells which are capable of differentiating in culture to endothelial cells and mesenchymal cells, the method comprising the steps of:
   (i) co-culturing primate embryonic stem (ES) or induced pluripotent stem (iPS) cells with OP9 bone marrow stromal cells for at least two to three days;
   (ii) depleting OP9 bone marrow stromal cells from the co-culture;
   (iii) sorting the co-cultured cells expressing APLNR$^+$ cell population; and
   culturing the APLNR$^+$ cells in a semi-solid culture medium comprising bFGF, wherein a subset of APLNR$^+$ cells are capable of differentiating in culture to endothelial cells and mesenchymal cells.

4. The method of claim 1, wherein the APLNR$^+$ cells further express at least one of platelet derived growth factor receptor alpha (PDGFRA) and kinase domain region (KDR).

5. A method of generating a population of primate cells expressing APLNR capable of forming mesenchymal stem cells, the method comprising:
   (i) co-culturing primate embryonic stem (ES) or induced pluripotent stem (iPS) cells with OP9 bone marrow cells for 2 days;
   (ii) depleting the OP9 cells from the cells obtained in step (i); and
   (iii) culturing the cells obtained in step (ii) in semisolid media and bFGF for 2-3 days to obtain colonies, wherein the colonies are capable of giving rise to mescenchymal stem cells.

6. A method of generating a population of primate cells expressing APLNR with hematopoietic and endothelial potential, the method comprising:
   (i) co-culturing primate embryonic stem (ES) or induced pluripotent stem (iPS) cells with OP9 bone marrow cells for 3 days;
   (ii) depleting the OP9 cells from the cells obtained in step (i); and
   (iii) culturing the cells obtained in step (ii) in semisolid media and bFGF for 2-3 days to obtain colonies, wherein the colonies are capable of giving rise to endothelial or hematopoietic cells.

* * * * *

UNITED STATES PATENT AND TRADEMARK OFFICE
CERTIFICATE OF CORRECTION

| | |
|---|---|
| PATENT NO. | : 9,771,561 B2 |
| APPLICATION NO. | : 14/569130 |
| DATED | : September 26, 2017 |
| INVENTOR(S) | : Maksym A. Vodyanyk et al. |

It is certified that error appears in the above-identified patent and that said Letters Patent is hereby corrected as shown below:

In the Specification

Column 3, Line 2, "feeder" should read --(i.e., feeder--.

Signed and Sealed this
Twentieth Day of August, 2019

Andrei Iancu
*Director of the United States Patent and Trademark Office*